(12) United States Patent
Basheer et al.

(10) Patent No.: US 10,280,389 B2
(45) Date of Patent: May 7, 2019

(54) ENZYMATIC TRANSESTERIFICATION/ESTERIFICATION PROCESSES EMPLOYING LIPASES IMMOBILIZED ON HYDROPHOBIC RESINS IN THE PRESENCE OF WATER SOLUTIONS

(71) Applicant: Trans Biodiesel Ltd., Shfaram (IL)

(72) Inventors: Sobhi Basheer, Sakhnine (IL); Usama Mohsen, Ibleen (IL)

(73) Assignee: TRANS BIODIESEL LTD., Shfaram (IL)

(*) Notice: Subject to any disclaimer, the term of this patent is extended or adjusted under 35 U.S.C. 154(b) by 0 days.

(21) Appl. No.: 14/143,258

(22) Filed: Dec. 30, 2013

(65) Prior Publication Data

US 2014/0186908 A1  Jul. 3, 2014

Related U.S. Application Data

(60) Provisional application No. 61/747,618, filed on Dec. 31, 2012.

(51) Int. Cl.

| | |
|---|---|
| *C12N 11/08* | (2006.01) |
| *C12M 1/40* | (2006.01) |
| *C12M 1/12* | (2006.01) |
| *C12M 1/06* | (2006.01) |
| *C12M 1/00* | (2006.01) |
| *C12M 1/34* | (2006.01) |
| *C12P 7/64* | (2006.01) |
| *C12M 1/02* | (2006.01) |

(52) U.S. Cl.
CPC ............ *C12M 21/18* (2013.01); *C12M 23/58* (2013.01); *C12M 25/02* (2013.01); *C12M 25/20* (2013.01); *C12M 27/02* (2013.01); *C12M 29/00* (2013.01); *C12M 29/18* (2013.01); *C12M 41/12* (2013.01); *C12M 41/22* (2013.01); *C12M 41/44* (2013.01); *C12M 47/10* (2013.01); *C12N 11/08* (2013.01); *C12P 7/649* (2013.01); *C12P 7/6436* (2013.01); *C12Y 301/01003* (2013.01); *Y02E 50/13* (2013.01)

(58) Field of Classification Search
None
See application file for complete search history.

(56) References Cited

U.S. PATENT DOCUMENTS

| | | | | |
|---|---|---|---|---|
| 4,209,591 | A * | 6/1980 | Hendriks | ........ B01J 8/20 435/294.1 |
| 7,790,429 | B2 | 9/2010 | Basheer | |
| 2001/0019731 | A1* | 9/2001 | Shindo | ........ C12C 11/07 426/11 |
| 2006/0063241 | A1 | 3/2006 | Chou | |
| 2010/0015676 | A1 | 1/2010 | Kreitschmann et al. | |
| 2010/0035312 | A1 | 2/2010 | Basheer | |
| 2010/0173370 | A1 | 7/2010 | Chou | |
| 2010/0209982 | A1 | 8/2010 | Basheer | |
| 2010/0330629 | A1 | 12/2010 | Basheer et al. | |
| 2013/0052701 | A1 | 2/2013 | Basheer et al. | |

FOREIGN PATENT DOCUMENTS

| | | | | |
|---|---|---|---|---|
| EP | 1840203 A1 | * | 10/2007 | ............ C12P 7/6436 |
| EP | 1840203 A1 | | 10/2007 | |
| WO | WO-8303844 A1 | * | 11/1983 | ............... C11C 3/08 |
| WO | 97/01632 A1 | | 1/1997 | |
| WO | 2008/084470 A2 | | 7/2008 | |
| WO | 2008/139455 A2 | | 11/2008 | |
| WO | 2009069116 A2 | | 6/2009 | |
| WO | WO-2010049491 A1 | * | 5/2010 | ............. C12P 7/649 |
| WO | 2011/107977 A1 | | 9/2011 | |
| WO | WO 2011107977 A1 | * | 9/2011 | ............. C11C 3/003 |
| WO | WO-2011107977 A1 | * | 9/2011 | ............. C11C 3/003 |
| WO | 2013/030816 A1 | | 3/2013 | |

OTHER PUBLICATIONS

Kosugi et al., Biotechnology and Bioengineering, vol. 36, pp. 617-622 (1990).*
Ricca et al., Asia-Pacific Journal of Chemical Engineering, vol. 4, pp. 365-368 (2009) (of record).*
Kosugi et al., Biotechnology and Bioengineering, vol. 36, pp. 617-622 (1990) (of record).*
Grosova et al., Czech Journal of Food Science, vol. 26, No. 1, pp. 1-14 (2008).*
Yu et al., Bioresource Technology, vol. 124, pp. 8-17 (2012).*
Sotoft, L.F. et al.,"Process simulation and economical evaluation of enzymatic biodiesel production plant", Bioresource Technology 101, pp. 5266-5274, vol. 101, (2010).
Hama, S. et al., "Enzymatic packed-bed reactor integrated with glycerol-separating system for solvent-free production of biodiesel fuel", Biochemical Engineering Journal, pp. 66-71, vol. 55, (2011).
Hilterhaus, L. et al., "Reactor Concept for lipase-Catalyzed Solvent-Free Conversion of Highly Viscous Reactants Forming Two-Phase Systems", Organic Process Research & Development, pp. 618-625, vol. 12, (2008).
Ricca, E. et al., "Olive husk oil transesterification in a fluidized bed reactor with immobilized lipases", Asia-Pacific Journal of Chemical Engineering, pp. 365-368, vol. 4, (2009).
Canilha et al Biocatalisadores imobilizados—use de celulas e enzimas imobilizadas em processos biotecnologicos; Biotecnologia Ciencia e Desenvolvimento ano IX, No. 36, p. 48-57 (2006).

(Continued)

*Primary Examiner* — Soren Harward
*Assistant Examiner* — Paul D. Pyla
(74) *Attorney, Agent, or Firm* — Browdy and Neimark, PLLC

(57) ABSTRACT

Disclosed are processing systems and processes for carrying out enzymatic batchwise or continuous process for the production of fatty acid alkyl esters for use in the biofuels, food and detergent industries.

21 Claims, 5 Drawing Sheets

(56) References Cited

OTHER PUBLICATIONS

Office Action, dated Jul. 16, 2015 in corresponding Brazilian application BR102013033923-7.
Chaplin and Bucke, "Enzyme Technology," Cambridge University Press, 1990.
W.M. Willis and A.G. Marangoni, Enzymatic Interesteritication, in: Food Lipids—Chemistry, Nutrition, and Biotechnology, edited by C.C. Akoh and D.B. Min, pp. 839-875 (2002).

* cited by examiner

ENZYMATIC TRANSESTERIFICATION/ESTERIFICATION PROCESSES EMPLOYING LIPASES IMMOBILIZED ON HYDROPHOBIC RESINS IN THE PRESENCE OF WATER SOLUTIONS

TECHNOLOGICAL FIELD

The presently disclosed subject matter relates to processing systems and processes for the production of fatty acid alkyl esters for use for example in the biofuels, food and detergent industries.

PRIOR ART

References considered to be relevant as background to the presently disclosed subject matter are listed below:
  WO11/107,977
  Co-pending international patent application PCT/IL2011/000699
  Ricca, E. et al., Asia-Pac. J. Chem. Eng. 2009; 4: 365-368
  Hilterhaus, L. et al., Organic Process Res. Develop. 2008, 12618-625
  Sotoft, L. F. et al., Bioresource Technol. 2010, 101:5266-5274
  Hama, S. et al., Biochem. Eng. J. 2011, 55:66-71

Acknowledgement of the above references herein is not to be inferred as meaning that these are in any way relevant to the patentability of the presently disclosed subject matter.

BACKGROUND

Enzymatic production of biofuels (biodiesel) is generally conducted in multiphasic systems, and is a complex process. The reaction is a transesterification/esterification reaction, in which a fatty acid source (e.g. oil) and an alcohol or alcohol donor, are reacted in the presence of a lipase (or phospholipase) preparation, specifically immobilized lipase/phospholipase preparation, as disclosed, for example in applicant's WO11/107,977 and co-pending international patent application PCT/IL2011/000699.

Immobilization of enzymes has been described by a vast number of techniques basically aiming at reducing the cost contribution of enzymes in the overall enzymatic process; facilitating recovery of enzymes from the products; and enabling continuous operation of the process. Also the above WO11/107,977 and co-pending PCT/IL2011/000699 disclose techniques for immobilizing lipases/phospholipases. Generally, the immobilization techniques employ physical adsorption of enzymes to solid supports, such as silica and insoluble polymers; adsorption on ion-exchange resins, covalent binding of enzymes to a solid support material, such as epoxidated inorganic or polymeric supports, entrapment of enzymes in a growing polymer, confinement of enzymes in a membrane reactor or in semi-permeable gels or cross-linking enzyme crystals (CLECS's) or aggregates (CLEAS's). A main issue is to produce immobilized enzyme preparations which would be stable, whilst effective, so as to be used over a large number of reaction cycles, since the immobilized enzymes are expensive, and a cost-affecting parameter in all method of production using them.

Lipases and phospholipases exhibit low tolerance towards hydrophilic substrates, in particular short-chain alcohols and short-chain fatty acids (below $C_4$). It has been observed in many research studies that short-chain alcohols and short-chain fatty acids, such as methanol and acetic acid, respectively, are responsible for detaching essential water molecules from the quaternary structure of those enzymes, leading to their denaturation and consequently loss of their catalytic activity. This drawback has prohibited the application of lipases for production of commercial quantities of fatty acids methyl esters ("biodiesel") using oil triglycerides and methanol as substrates.

In this above described reaction of transesterification/esterification of a fatty acid source with a free alcohol, the formed glycerol and water by-products generally accumulate on the biocatalyst and/or its vicinity, blocking the substrates from free access to the active site of the immobilized enzyme. Such biocatalysts generally lose their catalytic performance after a few cycles when the same batch of biocatalyst is used. The special immobilized enzyme preparations, exhibiting good stability over many production cycles, persisting activity. Examples of such enzyme preparations are disclosed, inter alia, in applicant's WO/2008/084470, WO/2008/139455 and WO2009/069116.

Conditions under which the catalytic reaction is carried out, can adversely affect the stability and efficiency of immobilized enzyme preparations. It is important to have enzyme preparations which retain stability and activity under the reaction conditions.

Considering the factors which determine the reaction rates, the possibility to re-use the enzymes, etc., some of which are described above, the choice of the reactor is important. Applicant's WO11/107,977 and co-pending PCT/IL2011/000699 discloses a stirred tank reactor (STR), in order to obtain high yield and maintain the stability of the immobilized enzymes preparations.

Most biodiesel production studies with immobilized enzymes have reported the use of stirred tank reactors (STR), operated batchwise or in a continuous mode. Immobilized enzymes are mechanically stirred in a tank reactor containing a screen for retaining the enzyme for multiple use. Such a system has been found to be useful for achieving dispersion of the immobilized enzyme in the reactor; however due to high shear, resin-immobilized enzymes might be susceptible to attrition, leading to loss of the enzyme activity. Very few research studies have studied the use of immobilized enzymes also in a packed bed reactor (PBR). The glycerol byproduct, formed in the transesterification/esterification reaction was removed periodically from the PBR to prevent clogging the system. Such a system has been used at laboratory scale, but not at large or industrial scale where high pressure drop can be developed over the PBR which leads to inhibition of the continuous operation of the PBR.

In order to improve mass transfer for substrates and also avoid pressure drop in the system, co-solvents have been used by different work studies.

Other types of reactors including fluidized bed reactor (FBR), bubble column reactor (BCR) and expanded bed reactor (EBR) have not been evaluated nor suggested for the production of biodiesel with the aid of immobilized enzymes, and in any case such reactors are conventionally considered unsuitable for this purpose due problems associated therewith, including for example low conversions and loss of catalytic activity in the product stream (Sotoft et al., 2010, ibid.).

GENERAL DESCRIPTION

Disclosed herein is processing system for the transesterification/esterification of a fatty acid with an alcohol, to form fatty acid alkyl esters, comprising a reaction vessel configured for reacting a reaction medium including a fatty acid source and at least one of an alcohol and an alcohol donor in the presence of an immobilized lipase preparation, wherein the immobilized lipase preparation comprises at least one lipase immobilized on a hydrophobic porous support and wherein said processing system is configured for passing the reaction medium through said immobilized lipase preparation in a direction at least partially opposed to gravity.

In at least one embodiment of the disclosed subject matter, the processing system can be configured for providing an expanded or fluidized bed of said immobilized lipase preparation.

In the above or other embodiments of the disclosed subject matter, said reaction vessel in the disclosed processing system can comprise a vessel inlet port and a vessel outlet port, and said vessel inlet port can be at a location lower than that of said vessel outlet port. Further, said reaction vessel can comprise a stirring system for stirring the reaction medium and said immobilized lipase preparation within the reaction vessel. Still further, said reaction vessel can comprise the immobilized lipase preparation, at least during operation of said processing system for the production of said fatty acid alkyl esters. Yet further, said reaction vessel can comprise the fatty acid source and the at least one of an alcohol and an alcohol donor, at least during operation of the processing system for the production of said fatty acid alkyl esters.

In the above or other embodiments of the presently disclosed subject matter, the said reaction medium in the disclosed processing system can comprise at least one of an aqueous alkaline buffer solution and water, said water being at least one of free water and mixed with a polyol or polyols, at least during operation of said processing system for the production of said fatty acid alkyl esters. Further the said reaction medium comprises a mixture, said processing system comprising a pre-reaction vessel in selective fluid communication with said reaction vessel via said vessel inlet port, said pre-reaction vessel being configured for premixing at least the fatty acid source and the at least one of an alcohol and an alcohol donor to form said mixture, and for selectively delivering said mixture to said reaction vessel at least during operation of said processing system for the production of said fatty acid alkyl esters.

In the above or other embodiments of the presently disclosed subject matter, the said processing system further comprises a supply of fatty acid source in selective fluid communication with said pre-reaction vessel and configured for selectively delivering the fatty acid source to said pre-reaction vessel at least during said operation of said processing system, and an alcohol source in selective fluid communication with said pre-reaction vessel and configured for selectively delivering the at least one of an alcohol and an alcohol donor to said pre-reaction vessel at least during said operation of said processing system.

In the above or other embodiments of the presently disclosed subject matter, the said processing system further optionally comprising at least one of an aqueous buffer source and a water source in selective fluid communication with said pre-reaction vessel and configured for selectively delivering the at least one of an aqueous alkaline buffer solution and water, free or mixed with a polyol/polyols, to said pre-reaction vessel, to be included in said reaction mixture at least during said operation of said processing system. The said processing system can be configured for selectively delivering one or more of the fatty acid source and the at least one of an alcohol and an alcohol donor to said pre-reaction vessel in a continuous manner or in discrete batches at least during said operation of said processing system. Further, the said processing system can be configured for selectively delivering the at least one of an aqueous alkaline buffer solution and water, free or mixed with a polyol/polyols, to said pre-reaction vessel in a continuous manner or in discrete batches at least during said operation of said processing system. The said pre-reaction vessel in embodiments of the disclosed processing system can be configured for selectively delivering said mixture to said reaction vessel in a continuous manner or in discrete batches at least during said operation of said processing system.

In the above or other embodiments of the presently disclosed subject matter, the disclosed processing system can be configured for selectively and directly delivering to said reaction vessel at least one of the fatty acid source; and/or the at least one of an alcohol and an alcohol donor; and/or the at least one of an aqueous alkaline buffer solution and water, free or mixed with a polyol/polyols.

In the above or other embodiments of the presently disclosed subject matter, the said reaction vessel can comprise a thermal regulation processing system configured for maintaining the reaction medium in said reaction vessel within a selected temperature range.

In the above or other embodiments of the presently disclosed subject matter, the said processing system can further comprise a retaining arrangement configured for retaining the immobilized lipase preparation within said reaction vessel at least during operation of said processing system. The said retaining arrangement can be at one or both of said reaction vessel outlet and said reaction vessel inlet.

In the above or other embodiments of the presently disclosed subject matter, the said processing system further comprises a product separation vessel in selective fluid communication with said reaction vessel, said processing system being configured for selectively delivering a reaction mixture including reaction products from said reaction vessel to said product separation vessel, and wherein said product separation vessel is configured for selectively separating a yield of the fatty acid alkyl esters from the reaction mixture delivered thereto. The said product separation vessel can comprise one of a centrifuge and gravity separation processing system.

In the above or other embodiments of the presently disclosed subject matter, in the said processing system said reaction vessel can be configured for selectively delivering said reaction mixture to said product separation vessel in a continuous manner or in discrete batches at least during said operation of said processing system.

In the above or other embodiments of the disclosed subject matter, the processing system can be configured for selectively dispensing said yield of fatty acid alkyl esters from said product separation vessel. Further, the said processing system can be configured for selectively delivering said yield of fatty acid alkyl esters from said product separation vessel in a continuous manner or in discrete batches. Yet further, the said processing system can be configured for increasing said yield of the fatty acid alkyl esters from the reaction mixture delivered to said product separation vessel. Still further, the said processing system is configured for selectively rerouting said yield of the fatty acid alkyl esters to said reaction vessel to further increase said yield of the fatty acid alkyl esters from the reaction mixture subsequently delivered to said product separation vessel. The said processing system can also be configured for selectively rerouting said yield of the fatty acid alkyl esters to an auxiliary reactor module, wherein said auxiliary reactor module comprises an auxiliary reactor vessel and an auxiliary product separation vessel, wherein said further increased yield of the fatty acid alkyl esters is selectively subsequently delivered via said auxiliary product separation vessel.

In the above or other embodiments of the presently disclosed subject matter, the said auxiliary reaction vessel in the disclosed processing system can be configured for reacting said yield of the fatty acid alkyl esters in the presence of an immobilized lipase preparation, wherein the immobilized lipase preparation comprises at least one lipase immobilized on a hydrophobic porous support and wherein said processing system is configured for passing the reaction medium through said immobilized lipase preparation in said auxiliary reaction vessel in a direction at least partially opposed to gravity.

In the above or other embodiments of the presently disclosed subject matter, the said processing system can be configured for selectively outputting and rerouting a reaction mixture including said reaction products back to said reaction vessel for further processing therein for enhancing yield of said fatty acid alkyl esters.

In the above or other embodiments of the presently disclosed subject matter, the said processing system can be configured for selectively outputting and rerouting a reaction mixture including said reaction products back to said reaction vessel and for selectively subsequently outputting and delivering a modified reaction mixture including reaction products to said product separation vessel, and wherein said product separation vessel is configured for selectively separating a yield of the fatty acid alkyl esters from the reaction mixture delivered thereto. Further, said processing system can be configured for rerouting the reaction mixture through said reaction vessel in a direction at least partially opposed to gravity. The disclosed processing can be configured for selectively outputting and rerouting a reaction mixture provided by said auxiliary reaction vessel back to said auxiliary reaction vessel for enhancing yield of said fatty acid alkyl esters. The said processing system can be configured for selectively outputting and rerouting a reaction mixture including said reaction products provided by said auxiliary reaction vessel back to said auxiliary reaction vessel and for selectively subsequently outputting and delivering a modified reaction mixture including reaction products from said auxiliary reaction vessel to said auxiliary product separation vessel, and wherein said auxiliary product separation vessel is configured for selectively separating a yield of the fatty acid alkyl esters from the reaction mixture delivered thereto.

In the above or other embodiments of the presently disclosed subject matter, the said processing system can be configured for passing the reaction products through said auxiliary reaction vessel in a direction at least partially opposed to gravity.

In the above or other embodiments of the presently disclosed subject matter, the said processing system can comprise one or more of the following features, in any desired combination or permutation:

A. The reaction vessel can comprise the immobilized lipase preparation, at least during operation of said processing system for the production of said fatty acid alkyl esters.
B. Additionally or alternatively to feature A, the reaction vessel can comprise the fatty acid source and the at least one of an alcohol and an alcohol donor, at least during operation of said processing system for the production of said fatty acid alkyl esters.
C. Additionally or alternatively to features A or B, said reaction medium comprises a mixture, said processing system further comprising a pre-reaction vessel in selective fluid communication with said reaction vessel, said pre-reaction vessel being configured for premixing at least the fatty acid source and the at least one of an alcohol and an alcohol donor to form said mixture, and for selectively delivering said mixture to said reaction vessel at least during operation of said processing system for the production of said fatty acid alkyl esters. The processing system can optionally further comprise a fatty acid source in selective fluid communication with said pre-reaction vessel and configured for selectively delivering the fatty acid source to said pre-reaction vessel at least during said operation of said processing system, and an alcohol source in selective fluid communication with said pre-reaction vessel and configured for selectively delivering the at least one of an alcohol and an alcohol donor to said pre-reaction vessel at least during said operation of said processing system. The processing system can optionally further comprise a buffer source in selective fluid communication with said pre-reaction vessel and configured for selectively delivering the at least one of an aqueous alkaline buffer solution and water (or water solution as defined herein) to said pre-reaction vessel to be included in said mixture at least during said operation of said processing system.
D. Additionally or alternatively to features A to C, the processing system can be configured for selectively delivering one or more of the fatty acid source and/or the at least one of an alcohol and an alcohol donor and/or the at least one of an aqueous alkaline buffer solution and water (or water solution as defined herein) to said pre-reaction vessel each in either a continuous manner or in discrete batches, at least during said operation of said processing system.
E. Additionally or alternatively to features A to D, the pre-reaction vessel can be configured for selectively delivering said mixture to said reaction vessel in a continuous manner and/or in discrete batches at least during said operation of said processing system.
F. Additionally or alternatively to features A to E, the processing system can be configured for selectively and directly delivering to said reaction vessel at least one of the fatty acid source; the at least one of an alcohol and an alcohol donor; and the at least one of an aqueous alkaline buffer solution and water (or water solution as defined herein).
G. Additionally or alternatively to features A to F, the reaction vessel can comprise a thermal regulation processing system configured for maintain the reaction medium in said reaction vessel within a selected temperature range.
H. Additionally or alternatively to features A to G, the processing system can optionally further comprise a retaining arrangement configured for retaining the immobilized lipase preparation within said reaction vessel at least during operation of said processing system.
I. Additionally or alternatively to features A to H, the processing system further comprises a product separation vessel in selective fluid communication with said reaction vessel, said processing system being configured for selectively delivering a reaction mixture including reaction products from said reaction vessel to said product separation vessel, and wherein said product separation vessel is configured for selectively separating a yield of the fatty acid alkyl esters from the reaction mixture delivered thereto. For example, the product separation vessel can be one of a centrifuge and gravity separation processing system.
J. Additionally or alternatively to features A to I, the reaction vessel is configured for selectively delivering said reaction mixture to said product separation vessel in a continuous manner and/or in discrete batches at least during said operation of said processing system.

K. Additionally or alternatively to features I to J, the processing system is configured for selectively delivering said yield of fatty acid alkyl esters from said product separation vessel. For example, the processing system is configured for selectively delivering said yield of fatty acid alkyl esters from said product separation vessel in a continuous manner and/or in discrete batches.

L. Additionally or alternatively to features A to K, the processing system is configured for increasing said yield of the fatty acid alkyl esters from the reaction mixture delivered to said product separation vessel. In one configuration of the processing system having this feature, the processing system is configured for selectively rerouting said yield of the fatty acid alkyl esters to said reaction vessel to further increase said yield of the fatty acid alkyl esters from the reaction mixture subsequently delivered to said product separation vessel. In another configuration of the processing system having this feature, the processing system is configured for selectively rerouting said yield of the fatty acid alkyl esters to an auxiliary reactor module, wherein said auxiliary reactor module comprises an auxiliary reactor vessel and an auxiliary product separation vessel, wherein said further increased yield of the fatty acid alkyl esters is selectively subsequently delivered via said auxiliary product separation vessel.

M. The system comprises a reaction medium recirculation line feeding the reaction medium output from the top of the reactor vessel back into the bottom of the reactor vessel to flow thereafter through the reactor vessel towards the top of the reactor leading to provide expanding/fluidizing of the immobilized lipase preparation depending on the recirculation flow rate.

Also disclosed herein is a process for the transesterification/esterification of a fatty acid source with an alcohol, to form fatty acid alkyl esters, comprising reacting a reaction medium including a fatty acid source and an alcohol or an alcohol donor in the presence of an immobilized lipase preparation, wherein the immobilized lipase preparation comprises at least one lipase immobilized on a hydrophobic porous support and the reaction medium optionally stirred and contains at least one of an aqueous alkaline buffer solution and water, free or mixed with a polyol/polyols, and wherein the reaction medium is passed through said immobilized lipase preparation in a direction at least partially opposed to gravity. Reaction products of the disclosed process include said fatty acid alkyl esters. The disclosed process can further comprise the step of selectively directly recirculating said reaction products to said immobilized lipase preparation. In embodiments of the disclosed process, in said recirculating step, said reaction products are passed through said immobilized lipase preparation in a direction at least partially opposed to gravity. Said step of selectively directly recirculating reaction products of said reaction to said immobilized lipase preparation can be repeated a plurality of times. In embodiments of the process disclosed, the reaction can be carried out at a temperature between 0° C. and 100° C., specifically between 20-30° C.

In the above or other embodiments of the presently disclosed process, the said process can further comprise the step of selectively separating fatty acid alkyl esters from said reaction products.

In the above or other embodiments of the presently disclosed process, the said aqueous alkaline buffer solution can be a mild aqueous alkaline buffer solution with a pH of from about 7 to about 11, and said water can be in the form of a water solution of at least one of dissolved salts and polyol/polyols with a pH of from about 3 to about 11. The said at least one of aqueous alkaline buffer solution and water can be contained at a quantity of at least 0.01% wt. of the fatty acid source, particularly 2% wt. of the fatty acid source, more particularly 5% wt. of the fatty acid source.

In the above or other embodiments of the presently disclosed process, said alcohol can be a short-chain alcohol, specifically $C_1$-$C_6$ alkyl alcohol, more specifically $C_1$-$C_4$ alkyl alcohol, particularly methanol or ethanol, or said alcohol is a medium-chain fatty alcohol ($C_6$-$C_{10}$) or long-chain fatty alcohols ($C_{12}$-$C_{22}$). Further, the said alcohol donor can be a mono-alkyl ester, such as methyl acetate or a dialkyl carbonate, such as dimethyl carbonate, serving also as a source for mild alkaline reagent in the reaction medium.

In the above or other embodiments of the presently disclosed process, said at least one lipase can be a lipase derived from any one *Rhizomucor miehei, Pseudomonas* sp., *Rhizopus niveus, Mucor javanicus, Rhizopus oryzae, Aspergillus niger, Penicillium camembertii, Alcaligenes* sp., *Acromobacter* sp., *Burkholderia* sp., *Thermomyces lanuginosus, Chromobacterium viscosum, Candida antarctica* B, *Candida rugosa, Candida antarctica* A, papaya seeds and pancreatin.

In the above or other embodiments of the presently disclosed process, said immobilized lipase can catalyze the esterification of free fatty acids to yield fatty acid alkyl esters and water as by-product, and the transesterification of triglycerides and partial glycerides to yield fatty acid alkyl esters and glycerol as by-product.

In the above or other embodiments of the presently disclosed process, said lipase preparation can comprise at least two lipases which can be each separately immobilized on a hydrophobic support or co-immobilized on the same hydrophobic support, and wherein said lipases possess identical or different regio-specificity.

In the above or other embodiments of the presently disclosed process, said support can be any one of hydrophobic aliphatic polymer-based support and hydrophobic aromatic polymer-based support. Further, said support can be porous or non-porous inorganic support, which can be hydrophobic or is coated with hydrophobic organic material.

In the above or other embodiments of the presently disclosed process, said alkaline buffer solution can be added to said fatty acid source in a premixing stage or directly to the reaction medium.

In the above or other embodiments of the presently disclosed process, said fatty acid source can be any one of plant oil, animal fat, algal oil, fish oil, waste oil, grease trap and any mixtures thereof. More specifically, said fatty acid source can comprise free fatty acids, mono-, di- or triglycerides, their mixtures at any ratio, in the absence or presence of other minor fatty acid derivatives such as phospholipids and wax esters, more specifically said fatty acid source is unrefined, refined, bleached, deodorized or any of their combinations.

In the above or other embodiments of the presently disclosed process, where said alcohol is methanol said resulting fatty acid esters are fatty acid methyl esters (FAME—Biodiesel).

BRIEF DESCRIPTION OF THE DRAWINGS

In order to better understand the subject matter that is disclosed herein and to exemplify how it can be carried out in practice, embodiments will now be described, by way of non-limiting example only, with reference to the accompanying drawings, in which.

DETAILED DESCRIPTION

Figure 1:
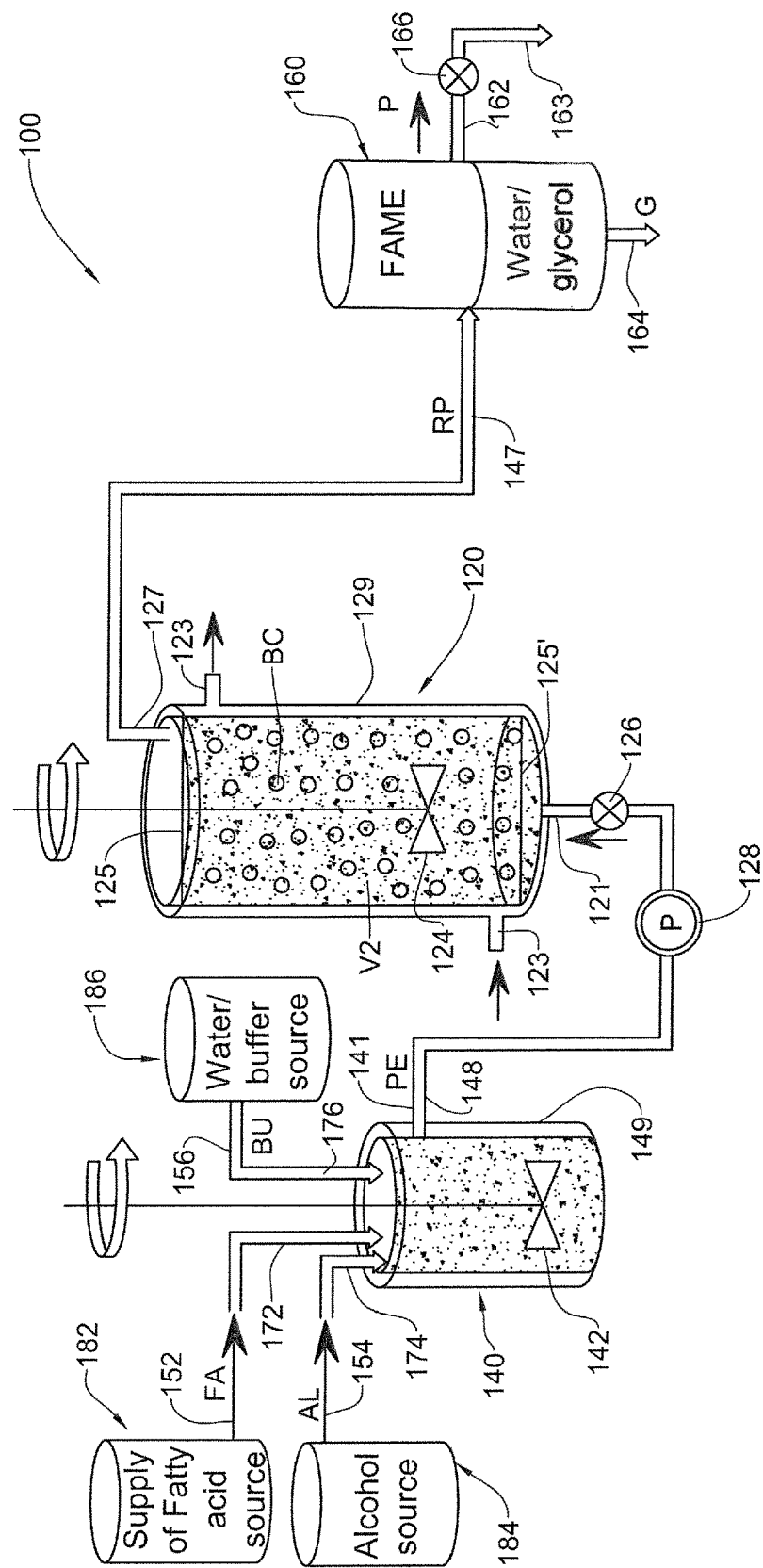
FIG. 1: illustrates schematically a first example of a processing system for the production of fatty acid alkyl esters according to an aspect of the presently disclosed subject matter.

Reactors conventionally used in the production of biodiesel can be Stirred Tank Reactors (STR), as described in applicant's WO2011/107977. Alternatively, Packed Bed Reactors (PBR) can be used. The multiphasic nature of the enzyme-catalyzed transesterification reaction is, conventionally, the factor to be accounted for when choosing the reactor, which should be a heterogeneous reactor.

The present inventors developed a novel processing system and corresponding reactor, which can be used, inter alia, in enzymatic production of fatty acid alkyl esters, specifically fatty acid methyl esters (biodiesel).

In at least one embodiment, the reactor incorporates therein elements of stirred tank reactors and expanded bed reactors, providing a stirred and expanded bed of immobilized enzyme (e.g. lipase preparation), and is thus referred to herein as a hybrid reactor.

In at least one embodiment, the reactor incorporates therein elements of stirred tank reactors and fluidized bed reactors, providing a stirred and fluidized bed of immobilized enzyme (e.g. lipase preparation), and is thus also referred to herein as a hybrid reactor.

In at least one embodiment, the reactor operates as an expanded bed (non-stirred) reactor, providing an expanded bed of immobilized enzyme (e.g. lipase preparation).

In at least one embodiment, the reactor operates as a fluidized bed (non-stirred) reactor, providing a fluidized bed of immobilized enzyme (e.g. lipase preparation).

At least some of the embodiments of the reactor disclosed herein, in particular the hybrid reactors, allow for fluidization/expansion of the enzyme beads in the reactor, and facilitate flow of the reaction medium significantly through the reactor, reducing potential risk of clogging of the respective processing system. In particular, it provides for an effect of enhanced reactor performance via increased exposure/contact time between the reactants and the biocatalysts, by avoiding packing of the enzyme bed and instead expanding or fluidizing the enzyme bed using a feed (and optionally a recirculation line). This effect is accomplished by providing the reaction medium through the reactor in a gravity opposed direction (for example from bottom to top), and optionally concurrently providing mechanical agitation of the enzyme bed. Further, expanding or fluidizing the enzyme resin by feeding and/or recirculating the reaction medium in a gravity opposed direction through the reactor is considered herein to prevent or at least significantly reduce sticking of the formed glycerol by-product onto the resin-immobilized enzyme, thus preventing or at least reducing clogging of the enzyme bed, and facilitating flow out of the reactor and the processing system. It is further considered that this effect can be enhanced by simultaneously mechanically stirring the enzyme bed with an agitator, for example while providing reaction medium (and optionally recirculating reaction products) through the reactor in a gravity opposed direction.

According to at least some aspects of the presently disclosed subject matter, the reaction medium is provided into the reactor in a direction therethrough that is not aligned with gravity, for example a partially or fully gravity-opposed direction or a horizontal direction.

According to an aspect of the presently disclosed subject matter there is provided a processing system for the production of fatty acid alkyl esters, specifically fatty acid lower methyl esters (biodiesel). Referring to FIG. 1, a first embodiment of such a processing system, generally designated with the reference numeral 100, comprises a reactor in the form of reactor vessel 120, a pre-reaction preparation vessel 140, and a product separation vessel 160.

Pre-reaction preparation vessel 140 is configured for receiving feedstock materials, and optionally at least one of an aqueous buffer solution and water (or water solution as defined herein), for forming a suitable emulsion therefrom, and for feeding the prepared emulsion PE (also referred to herein as emulsified feedstock) to the reactor vessel 120. In particular, such feedstock materials can include fatty acid source FA (for example waste cooking oil) from a supply of a fatty acid source 182, and alcohol AL (for example methanol) from alcohol source 184, and optionally at least one of an aqueous buffer and water (free or mixed with a polyol/polyols e.g. glycerol at different ratios) BU from optional buffer/water source 186, provided via suitable supply line 152, supply line 154, and optional supply line 156, respectively, each in fluid communication with said pre-reaction preparation vessel 140 via vessel inlets 172, 174, 176, respectively and suitable valves (not shown).

The pre-reaction preparation vessel 140 defines an internal volume V1 in which the reaction mixture, including feedstock materials and optionally buffer/water, provided therein via vessel inlets 172, 174, 176, are mixed together by means of a suitable stirring processing system 142, driven by a powered source (not shown), to form emulsion PE. The pre-reaction preparation vessel 140 comprises an outer jacket 149 through which a suitable work fluid can be circulated to maintain the volume V1 at a desired steady state temperature. For example, the work fluid can be, oil, water or any other suitable liquid or gas, heated or cooled in a different vessel (not shown) and pumped through the jacket 149 via suitable inlet and exit ports (not shown). In alternative variations of this embodiment, pre-reaction preparation vessel 140 can comprise a processing system of heating and/or cooling elements, for example electrically powered heating and/or cooling elements, instead of or in addition to the jacket 149. In yet other alternative variations of this embodiment, the thermal regulation processing system can be omitted.

Reactor vessel 120 is configured for receiving prepared emulsion PE from pre-reaction preparation vessel 140, for reacting the feedstock materials therein in the presence of a suitable biocatalyst BC (also referred to herein as an enzyme bed) to produce reaction products RP, and for feeding the reaction products RP from the reaction mixture to the product separation vessel 160. Outlet line 148 provides selective fluid communication between pre-reaction preparation vessel 140 and reactor vessel 120 via outlet 141, suitable valves 126, and allows the prepared emulsion PE prepared by the pre-reaction preparation vessel 140 to be selectively fed to the reactor vessel 120 as desired. Outlet line 148 can comprise a powered pump 128 to pump prepared emulsion PE to the reactor vessel 120; optionally, the outlet 141 is at a height greater than inlet 121, and preferably also outlet 127, and thus prepared emulsion PE flows to the reactor vessel 120 at least partially via gravity.

The reaction vessel 120 defines an internal volume V2 in which the prepared emulsion PE in the reaction mixture, provided therein via vessel inlet 121, is reacted.

In this embodiment, the reaction vessel 120 is a hybrid reactor, providing expansion or fluidization of the enzyme bed, with the option of selectively stirring the reaction mixture. The reaction mixture can be selectively stirred by means of a suitable stirring processing system 124, driven by a powered source (not shown) to form the reaction products RP. Stirring of the reaction mixture can be carried out concurrently with feeding the prepared emulsion PE into the reaction mixture within the reaction vessel 120, or independently thereof, for example when feeding of prepared emulsion PE into reaction vessel 120 is stopped, and stirring occurs of the reaction mixture already within the reaction vessel 120.

The biocatalyst BC can comprise, for example, a suitable enzyme and, in this and other embodiments, is provided in the form of immobilized enzyme beads which remain in the reactor vessel 120 until they become ineffective or are not sufficiently effective, whereupon they can be removed and replaced with new biocatalyst BC. For example, the biocatalyst BC can comprise lipase derived from any one of *Rhizomucor miehei, Mucor miehei, Pseudomonas* sp., *Rhizopus* sp., *Mucor javanicus, Penicillium roqueforti, Aspergillus niger, Chromobacterium viscosum, Acromobacter* sp., *Burkholderia* sp., *Candida antarctica* A, *Candida antarctica* B, *Thermomyces lanuginosus, Candida rugosa, Alcaligenes* sp., *Penicillium camembertii*, papaya seeds and pancreatin, but not limited thereto immobilized on a hydrophobic and porous polystyrene-divinylbenzene-based resin.

The reactor vessel 120 comprises a thermal regulation processing system in the form of an outer jacket 129 through which a suitable work fluid can be circulated to maintain the volume V2 at a desired steady state temperature. For example, the work fluid can be oil, water, or any other suitable liquid or gas or other fluid, heated or cooled in a different vessel (not shown) and pumped through the jacket 129 via suitable inlet and exit ports 123. In alternative variations of this embodiment, the thermal regulation processing system comprises a processing system of heating and/or cooling elements, for example electrically powered heating and/or cooling elements, instead of or in addition to the jacket 129. In yet other alternative variations of this embodiment, the thermal regulation processing system can be omitted.

The reactor vessel 120 comprises a suitable retaining arrangement in the form of filter 125' is provided downstream of the inlet 121 configured for preventing the biocatalyst BC from exiting reactor vessel 120 via inlet 121 or for clogging the inlet 121.

The reactor vessel 120 comprises an outlet 127, and a suitable retaining arrangement in the form of filter 125 is provided upstream of the outlet 127 configured for, filtering the reaction mixture, in particular the reaction products RP prior to being removed from reactor vessel 120, and for preventing the biocatalyst BC from being removed with the reaction products RP.

In alternative variations of this and other embodiment of the processing system, one or both of the filter 125 and filter 125' can be omitted. For example, the flow rate of reaction mixture through the reactor vessel 120 can be regulated to provide an expansion or fluidization of the enzyme bed such that the biocatalyst BC remains confined within the volume V2.

The vessel outlet 127 is spaced from the vessel inlet 121 in a direction generally opposed to the gravitational gradient, i.e., vessel inlet 121 is gravitationally below the vessel outlet 127. In this particular embodiment, the vessel inlet 121 is located at the lower part of vessel 120, in particular the bottom thereof, while the vessel outlet 127 is located at an upper part of the vessel 120. The vessel outlet 127 is horizontally spaced from the vessel inlet 121 in this embodiment, but can instead be aligned horizontally while being vertically spaced with respect to one another.

In an alternative variation of this embodiment, the vessel outlet 127 is horizontally spaced from the vessel inlet 121 but at the same vertical disposition, to enable the prepared emulsion PE to be fed horizontally through the reaction mixture in the reaction vessel 120, without the assistance of gravity. The flow of prepared emulsion PE through the reaction mixture in the reaction vessel 120, in a direction not assisted by gravity (i.e., in a direction at least partially opposed to gravity, or in a horizontal direction) is considered to provide expansion or fluidization of the biocatalyst BC in the reaction vessel 120, or to at least significantly increase expansion or fluidization of the biocatalyst BC in the reaction vessel 120 as compared to providing prepared emulsion PE through the reaction mixture in the reaction vessel 120, in a direction assisted by gravity. In at least some embodiments including this embodiment, the degree of expansion or fluidization provided in the reactor vessel 120 can depend on a number of factors including none or more of volume flow rate or mass flow rate through the reactor vessel 120; specific gravity of the biocatalyst BC; specific gravity of the reaction mixture; internal geometry of the reactor vessel 120, i.e. volume V2.

Figure 2:
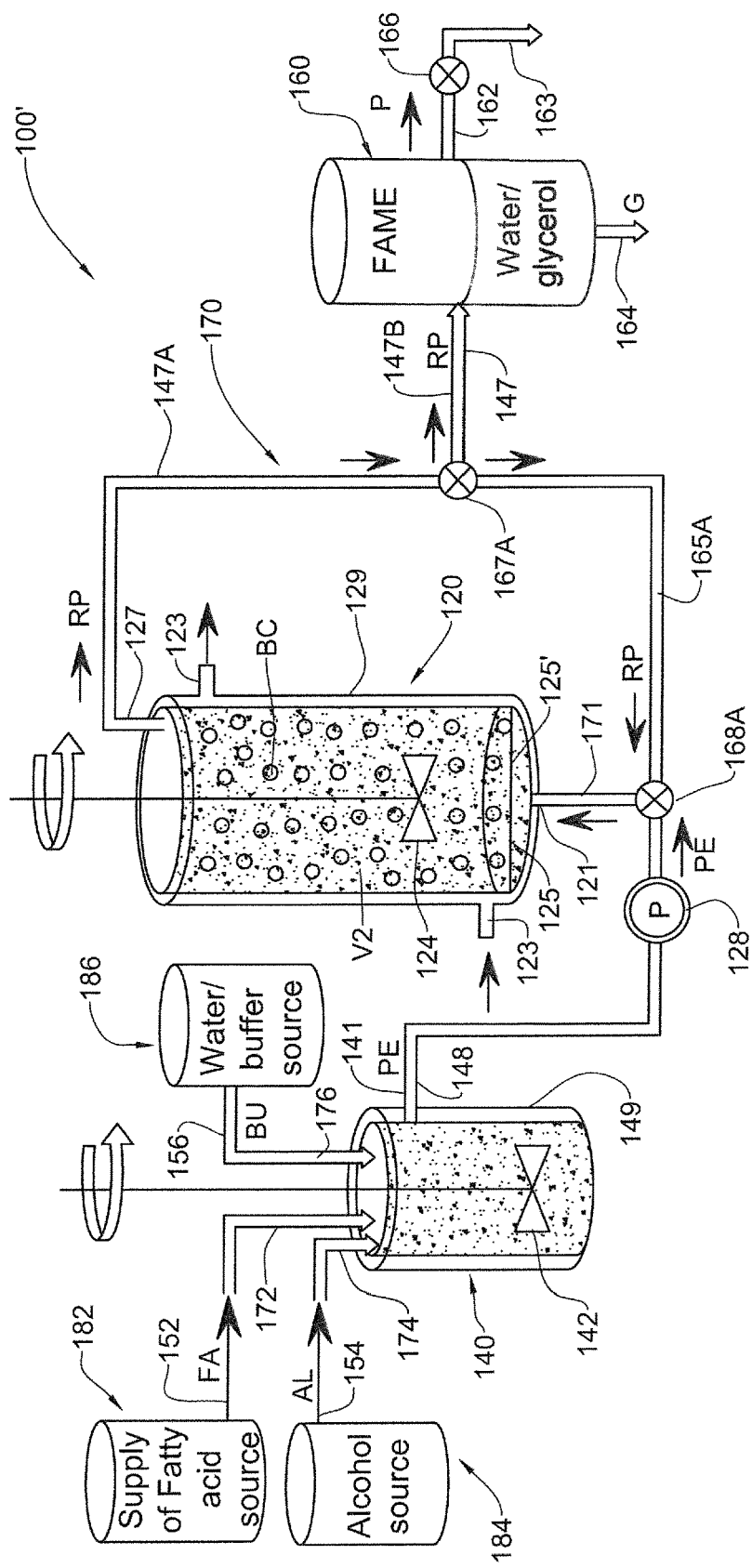
FIG. 2: illustrates schematically a second embodiment of a processing system for the production of fatty acid alkyl esters according to an aspect of the presently disclosed subject matter.
Figure 3:
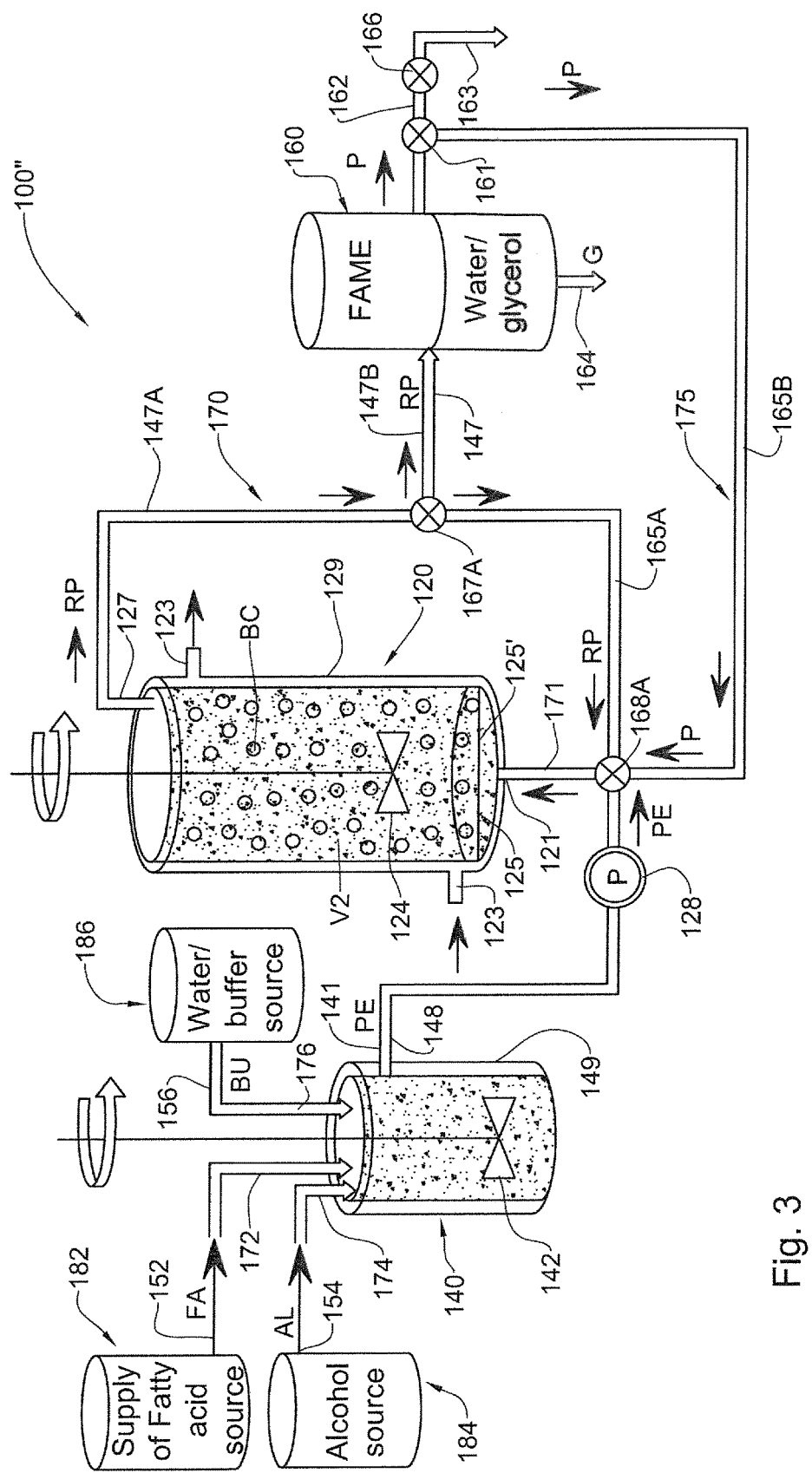
FIG. 3: illustrates schematically a third embodiment of a processing system for the production of fatty acid alkyl esters according to an aspect of the presently disclosed subject matter.

Particularly where the flow of prepared emulsion PE through the reaction mixture in the reaction vessel 120, is in a net horizontal direction through the reactor vessel 120, the processing system preferably includes recirculation line 170, as disclosed herein for the embodiments of FIGS. 2 and 3, for example.

Thus, in operation of the processing system 100, the prepared emulsion PE is pumped through the vessel 120 through inlet 121 and the reaction products RP are pumped out of the vessel 120 via outlet 127 partially or fully against the gravitational gradient, for example under the action of pump 128.

The product separation vessel 160 is configured for separating out, from the reaction products RP, the desired product P (fatty acid alkyl ester), from by-products including excess water and glycerol G. Outlet line 147 provides selective fluid communication between product separation vessel 160 and reactor vessel 120 via suitable valves (not shown) and allows the reaction products RP to be fed to the product separation vessel 160 from the reactor vessel 120 as desired. In this embodiment, the product separation vessel 160 comprises a centrifuge or gravity separation processing system for carrying out the aforesaid separation, and includes a first outlet interface 162 for outputting the product P, and a second outlet 164 for collecting the water and glycerol G (excess water and glycerol by-products or supplemented/originally present in the reaction medium. Product P can be collected via tap 163, for example.

The processing system 100 can thus be operated in a continuous production mode, in which prepared emulsion PE is fed into the reactor vessel 120, and the desired product P is collected in a continuous manner via tap 163. The emulsion PE can be prepared and delivered in a continuous manner to the lower part of reactor vessel 120 to top-up the volume of reactant therein at the same rate as the reaction products RP are being removed from outlet 127 at the upper part of reactor vessel 120. Optionally, the reaction mixture is continuously or intermittently stirred via stirring processing system 124 during such continuous operation; optionally the reaction mixture is not stirred during such continuous operation.

Alternatively, emulsion PE can be prepared and delivered in batches to the lower part of reactor vessel 120 to top-up the volume of reactant in the reaction mixture at discrete intervals whenever the level of reactants in the reactor vessel 120 drops to a particular minimum level following the continuous removal of reaction products RP via outlet 127 at the upper part of reactor vessel 120. Of course, additionally or alternatively, it is also possible to operate the processing system processing system 100 to provide the desired product P in batches rather than continuously. In any case, optionally, the reaction mixture in such batches is continuously or intermittently stirred via stirring processing system 124 during such batch-wise operations of the processing system 100; optionally the reaction mixture is not stirred during such batch-wise operation.

The inventors have found that spacing vessel outlet 127 from the inlet 121 in a direction opposed to the gravitational gradient can improve the operation of the reactor vessel 120, which is an unexpected and surprising effect.

Referring to FIG. 2, a second embodiment of the processing system, designated with reference numeral 100', is a variation of the first embodiment and thus includes all the elements and features as disclosed herein for the first embodiment of the processing system 100, mutatis mutandis. Processing system 100' is optionally configured for being operated in a first enhanced yield mode, wherein product P is, instead of being immediately and fully fed from outlet 127 to product separation vessel 160 and collected via tap 163, is instead partially or fully re-routed to the reactor vessel 120 via an optional first recirculation line 170 (also referred to herein interchangeably as an optional first rerouting processing system), including line 165A, vessel inlet 121 and valves 167A and 168A.

The valve 167A has an inlet or port connected to vessel outlet 127 via a first part of line 147, i.e., line 147A. The valve 167A has a first outlet or port connected to product separation vessel 160 via second part of line 147, i.e., line 147B, and a second outlet or port connected to reactor vessel 120 via line 165A, valve 168A and inlet 127. Recirculation line 170 is thus provided via line 147A, line 165A valve 167A, and line 171. Valve 168A can be provided to replace valve 126 or can operate in conjunction therewith. The second part of line 147, i.e., line 147B, can be omitted in cases where the valve 167A is connected directly to the product separation vessel 160.

Thus, valve 167A can be operated as a three-port valve to selectively control the relative proportions of the reaction products RP coming out of outlet 127 that are fed to the product separation vessel 160 and to reactor vessel 120, for example as follows:

valve 167A allows to fully divert all the reaction products RP away from product separation vessel 160 and towards reactor vessel 120;

valve 167A allows to fully divert all the reaction products RP into product separation vessel 160;

valve 167A allows to divert part of the reaction products RP to product separation vessel 160 and part of the reaction products RP into reactor vessel 120, the ratio of these two parts being selectively variable from zero to one;

valve 167A is closed, preventing flow of the reaction products RP to product separation vessel 160 and to reactor vessel 120.

In alternative variations of this embodiment, valve 167A can be replaced with a plurality of two-port valves or any other suitable valve arrangement to provide a similar selective control of the relative proportions of the reaction products RP (coming out of outlet 127) that are fed to the product separation vessel 160 and to reactor vessel 120. In yet other alternative variations of this embodiment, valve 167A recirculation line 170 can be replaced with line 147 and a control valve therein to selectively control flow of the reaction products RP exclusively to product separation vessel 160, plus an independent recirculation line and a control valve therein to selectively control flow of the reaction products RP exclusively to reactor vessel 120.

In the embodiment illustrated in FIG. 2, the valve 168A has an outlet or port connected to vessel inlet 121 via a line 171; a first inlet or port connected to line 165A; and a second inlet or port connected to pre-reaction preparation vessel 140 via line 148. The line 171 can be omitted in cases where the valve 168A is connected directly to the reactor vessel 120 at inlet 121.

Thus, valve 168A can be operated as a three-port valve to selectively control the relative proportion of the reaction products RP being fed into inlet 121 (and thus reactor vessel 120) via line 165A and the relative proportion of the prepared emulsion PE that is fed into the reactor vessel 120, for example as follows:

valve 168A allows prepared emulsion PE to be fed into the reactor 120 via inlet 121, while concurrently preventing the reaction products RP in line 165A from being fed into reactor vessel 120;

valve 168A allows the reaction products RP in line 165A to be fed into reactor vessel 120 via inlet 121, while concurrently preventing prepared emulsion PE from being fed into the reactor vessel 120 from the pre-reaction preparation vessel 140 (an additional powered pump can be required or desired in line 165A and/or line 147A, or the reaction products RP can flow in line 165A via gravity);

valve 168A allows part of prepared emulsion PE to be fed into the reactor 120 via inlet 121 while concurrently allowing part of the reaction products RP in line 165A to be fed into reactor vessel 120, the ratio of these two parts being selectively variable from zero to one;

valve 168A is closed, preventing flow of prepared emulsion PE into the reactor 120 via inlet 121, and preventing flow of reaction products RP in line 165A into reactor vessel 120.

When rerouted to reactor vessel 120, the respective proportion of reaction products RP, which include product P, can be further reacted therein with alcohol AL (optionally in the presence of buffer BU) already present in the reactor vessel 120. Optionally, alcohol AL can be provided to the re-routed reaction products RP directly, via a separate line (not shown) that directly connects source 184 to line 165A, and/or via a different alcohol source (not shown) connected to line 165A, and/or via a separate line (not shown) that indirectly connects source 184 (via pre-reaction preparation vessel 140) 184 to line 165A.

An effect of re-routing reaction products RP back to the reactor vessel 120 via the recirculation line 170 is to produce a higher yield of product P, which again can be separated out from byproducts using product separation vessel 160.

Additionally to the first enhanced yield mode, the processing system can be optionally configured for being selectively operated in a second enhanced yield mode. This enables the processing system to be selectively operated in the two enhanced yield modes (concurrently or sequentially or in any other manner), or for operating in only one enhanced yield mode (continuously, or in any manner). Alternatively, the processing system is not configured for operating in the first enhanced yield mode, but is instead configured for being selectively operated only in the second enhanced yield mode.

Thus, referring to FIG. 3, a third embodiment of the processing system, designated with the reference numeral 100" is an alternative variation of processing system 100 or of processing system 100', and, includes the elements and features as disclosed herein for processing system 100 and/or processing system 100', mutatis mutandis.

Processing system 100" is optionally configured for being operated in the second enhanced yield mode, wherein product P is, instead of being immediate collected via tap 163 when exiting the separation vessel 160, selectively re-routed to the reactor vessel 120 via an optional second recirculation line 175 (also referred to herein interchangeably as an optional second rerouting processing system). The second recirculation line 175 includes line 165B, valve 161, vessel inlet 121 and valve 168B, and line 171, which can be omitted in cases where the valve 168A is connected directly to the reactor vessel 120 at inlet 121. The valve 161 is upstream of first outlet interface 162, valve 166 and tap 163. The valve 161 can be selectively operated to divert the product P from tap 163 to the vessel 120 via second recirculation line 175. When rerouted to reactor vessel 120, the product P can be further reacted therein with alcohol AL, provided via a separate line (not shown) from source 184, from a different alcohol source (not shown), or from source 184 via pre-reaction preparation vessel 140, to produce a higher yield of product P, which again can be separated out from byproducts using product separation vessel 160. When the alcohol is provided via preparation vessel 140, the latter is first emptied of the prepared emulsion PE, and suitable valves prevent fatty acid source FA and optionally buffer/water being provided by supply 182 and source 186.

In the embodiment illustrated in FIG. 3, valve 168B is similar to (and thus effectively replaces) valve 168A of the embodiment of FIG. 2, mutatis mutandis, and further includes an additional, third inlet or port to allow selective connection of the valve 168B to valve 166 via line 165B. Valve 168B can be selectively operated as valve 168A, mutatis mutandis, or as a 4-way valve, for example as follows:

selectively allowing only one of the three lines 148, 165A, 165B to be connected to inlet 121 while preventing fluid communication between each of the other two lines and inlet 121;

selectively allowing any two of the three lines 148, 165A, 165B to be connected to inlet 121, while preventing fluid communication between the other line and inlet 121; the relative proportions of respective materials (prepared emulsion PE via line 148; product P via line 165B; reaction products RP via line 165A) flowing in the two selected lines can be as desired;

selectively allowing the three lines 148, 165A, 165B to be connected to inlet 121; the relative proportions of respective materials (prepared emulsion PE via line 148; product P via line 165B; reaction products RP via line 165A) flowing in the three selected lines can be as desired;

selectively closing all the inlets, thereby preventing fluid communication between each of the three lines 148, 165A, 165B and inlet 121.

Thus, by controlling operations of valves 167A and 168B, the processing system can be selectively operated in either the first enhanced yield mode, or the second enhanced yield mode, or in both enhanced yield modes, concurrently or sequentially or in any combination.

In an alternative variation of the embodiment of FIG. 3, the line 165A can be omitted, and thus the respective processing system can optionally and selectively operate in said second enhanced yield mode, but not in the aforesaid first enhanced yield mode.

In each of the embodiments of the processing system referred to above, suitable pumps and/or gravity feeds and additional controllable valves can be provided for selectively transporting the respective materials through one or more of the respective lines 152, 154, 156, 148, 147, 147A, 147B, 165A, 165B, 171, and a suitable controller (not shown) monitors and controls operation of the respective processing system.

In at least some alternative variations of the first, second or third embodiments, the pre-reaction preparation vessel 140 can be integral with the respective reactor vessel 120. For example, the respective internal volumes V1 and V2 can be separated by a wall having an opening arrangement corresponding to, and thus replacing, the line 148. Alternatively, the respective internal volumes V1 and V2 can be contiguous, but internal volume V1 is sufficiently spaced from the biocatalyst BC to provide sufficient time for the emulsion PE to form before reaching the biocatalyst BC. In any case, the respective pre-reaction preparation vessel 140 and the respective reactor vessel 120 are configured such that the emulsion PE is passed through volume V2 in a direction partially or fully opposed to the gravitational gradient.

In alternative variations of one or more of the above embodiments, one, two or all of the fatty acid source FA, alcohol AL, and optionally buffer/water BU can be provided directly to the reactor vessel 120, bypassing the pre-reaction preparation vessel 140. For example, one or more of the supply of fatty acid source 182, alcohol source 184, and buffer/water source 186, can be in selective fluid communication directly with reactor vessel 120 via suitable supply lines (not shown), in addition to adding water (free or mixed with a polyol/polyols e.g. glycerol at different ratios) or buffer solution via a separate line, bypassing the pre-reaction preparation vessel 140. In such cases at least the fatty acid FA, and optionally alcohol AL, and/or buffer/water BU, are provided at a lower part of the vessel 120 so that these materials pass vertically up through the vessel 120.

The processing system 100 according to the first, second or third embodiments, or alternative variations thereof, can optionally be modified to further optionally comprise an auxiliary reactor module for further enhancing the yield of the respective processing system.

Figure 4:
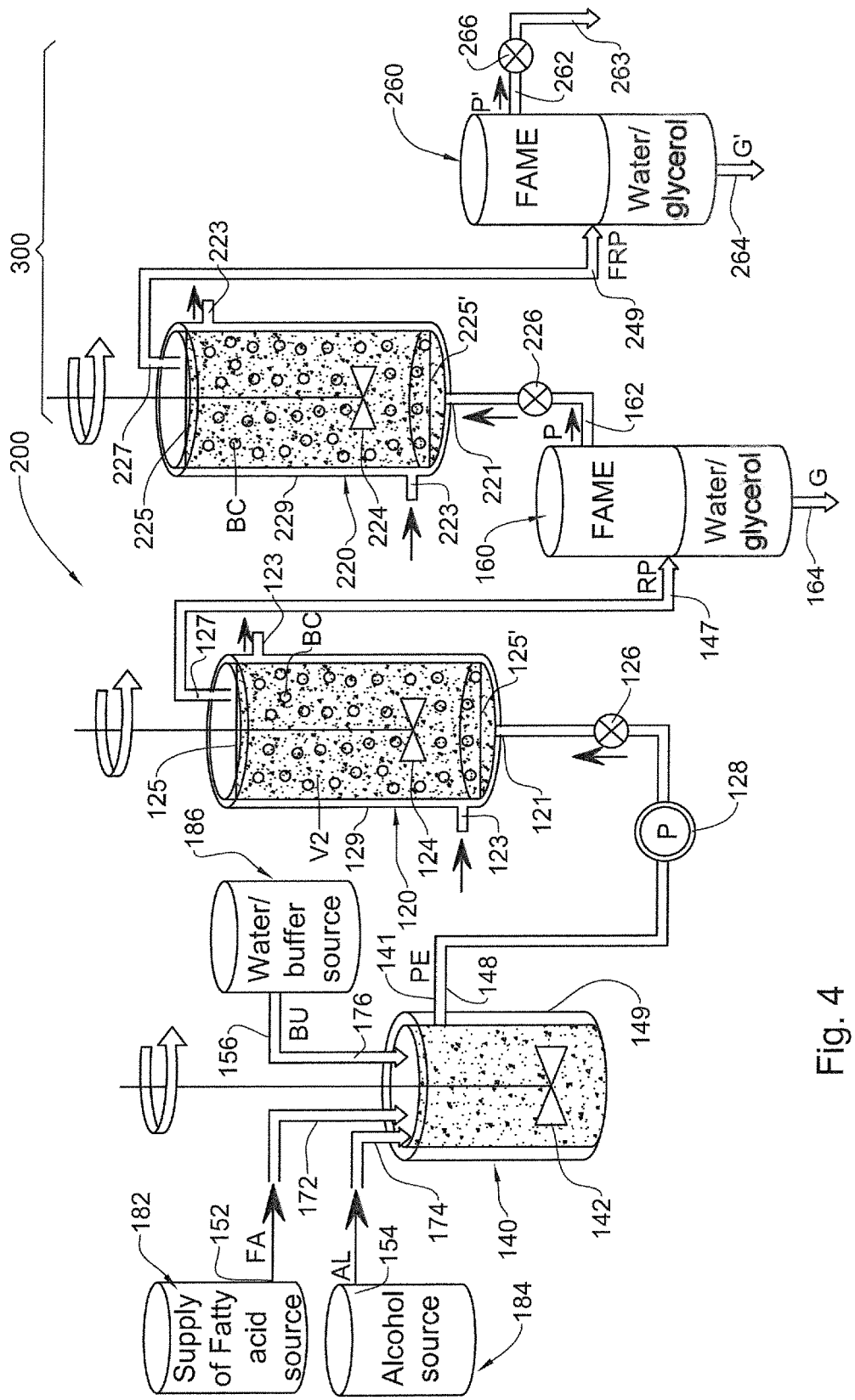
FIG. 4: illustrates schematically a fourth embodiment of a processing system for the production of fatty acid alkyl esters according to an aspect of the presently disclosed subject matter.

Referring to FIG. 4, a modified first embodiment of the processing system, also referred to herein as the fourth embodiment and designated with the reference number 200, comprises all the elements and features of the first embodiment, including alternative variations thereof, including all like-numbered components as in FIG. 1, mutatis mutandis, with some differences. For example processing system 200 also comprises: a reactor vessel 120, a pre-reaction preparation vessel 140, a product separation vessel 160, supply of fatty acid source 182, alcohol source 184, optional buffer/water source 186, supply lines 152, 154, 156, vessel inlets 172, 174, 176, stirring system 142, outer jacket 149, outlet line 148 vessel inlet 121, stirring system 124, biocatalyst BC outer jacket 129, inlet and exit ports 123, outlet 127, filter 125, filter 125', outlet line 147 first outlet interface 162 second outlet 164, valve 126; as disclosed for the first embodiment, the second embodiment, and the third embodiment, mutatis mutandis.

However, in the fourth embodiment, tap 163 and valve 166 of the first embodiment are omitted, and instead a first embodiment of the auxiliary reactor module 300 is operatively connected to the first outlet interface 162 of the product separation vessel 160.

Auxiliary reactor module 300 comprises an auxiliary reactor vessel 220 and an auxiliary product separation vessel 260, which in this embodiment are respectively substantially similar to the illustrated embodiment or variations thereof, of reactor vessel 120 and product separation vessel 160, as disclosed herein mutatis mutandis.

Thus, auxiliary reactor vessel 220 comprises vessel inlet 221, stirring system 224, biocatalyst BC, outer jacket 229, inlet and exit ports 223, outlet 227, filter 225, filter 225', respectively similar to reactor vessel 120 comprising vessel inlet 121, stirring system 124, biocatalyst BC, outer jacket 129, inlet and exit ports 123, outlet 127, filter 125, filter 125', as disclosed for the first embodiment, the second embodiment, and the third embodiment, or alternative variations thereof mutatis mutandis.

Thus, auxiliary product separation vessel 260 comprises first outlet interface 262, second outlet 264, valve 266 and tap 263, respectively similar to product separation vessel 160 comprising first outlet interface 162 second outlet 164, valve 166 and tap 163, as disclosed for the first embodiment, the second embodiment, and the third embodiment, or alternative variations thereof mutatis mutandis.

In operation, the desired product P from product separation vessel 160 is routed to the auxiliary reactor vessel 220 via line 267 (which connects to first outlet interface 162), valve 226 and vessel inlet 221. When routed to auxiliary reactor vessel 220, the product P can be further reacted therein with alcohol AL (optionally in the presence of at least one of water (free or mixed with a polyol/polyols e.g. glycerol at different ratios) and aqueous buffer solution) provided via a separate line (not shown) from source 184 or from a different alcohol source (not shown), to produce further reacted products FRP. Line 249 enables the further reacted products FRP to be transported from vessel outlet 227 to the auxiliary product separation vessel 260, which then operates to separate a higher yield of product P' from byproducts, which can be removed via valve 266 and tap 263. As with the reactor vessel 120, mutatis mutandis, the vessel outlet 227 is spaced from the vessel inlet 221 in a direction opposed to the gravitational gradient.

Processing system 200 can be operated in a similar manner to processing system 100, mutatis mutandis, with the main difference being that the product P, instead of being collected via tap 163 is further processed in auxiliary reaction vessel 220, and the further reacted products FRP are then transported to auxiliary separation vessel 260. In the auxiliary separation vessel 260 the desired enhanced yield product P' (fatty acid alkyl ester) in the further reacted products FRP are separated from by-products including excess water and glycerol G', and the enhanced yield product P' is then collected via tap 263.

It is to be noted that the processing system 100' according to the second embodiment, and/or the processing system 100" according to the third embodiment, can each be optionally modified to include auxiliary reactor module 300, in a similar manner to that disclosed herein for the first embodiment of the processing system 100 in the fourth embodiment of the processing system 200, mutatis mutandis, in which, essentially, in each case the respective valve 166 and tap 163 are removed, and replaced with auxiliary reactor module 300.

Figure 5:
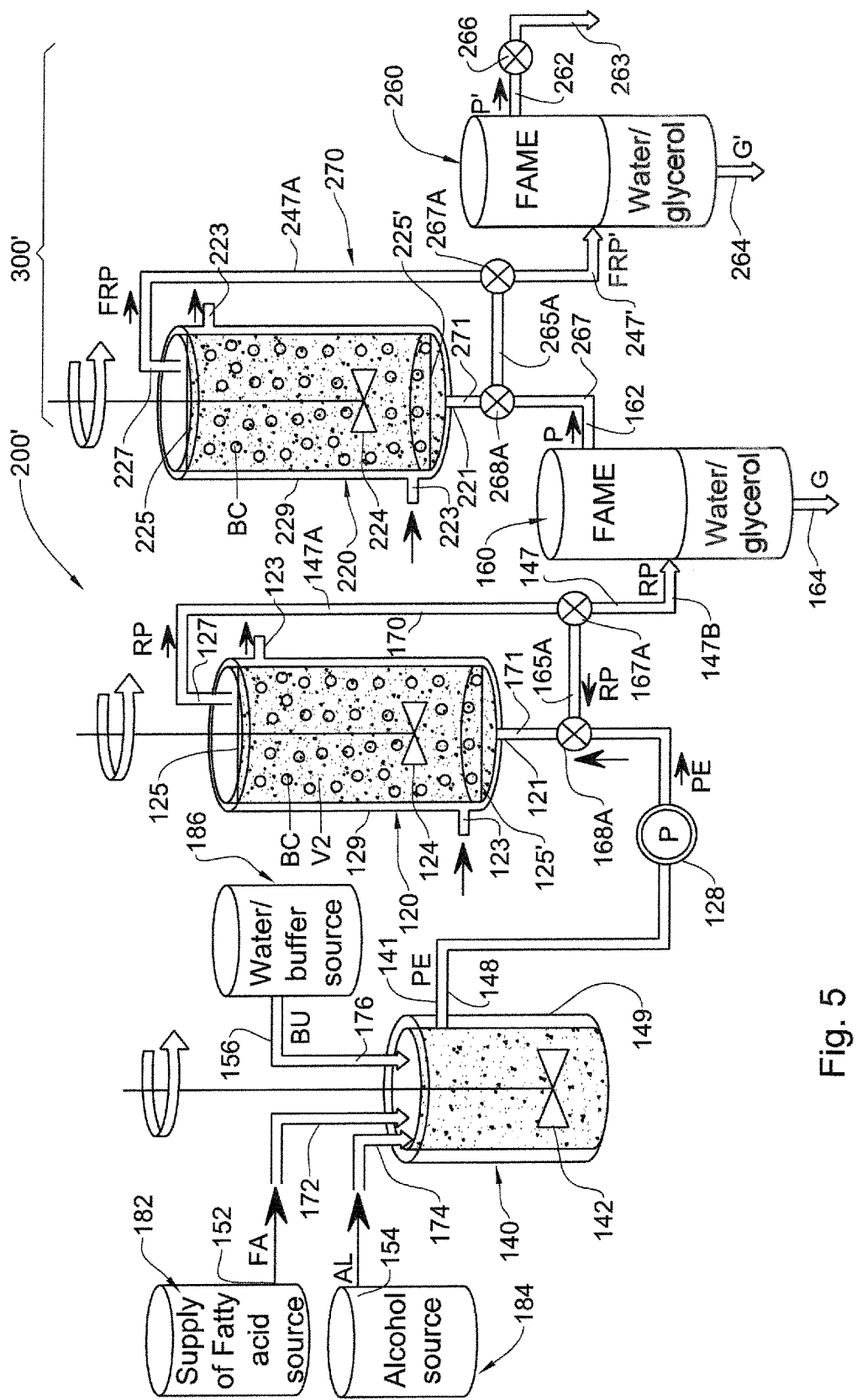
FIG. 5 illustrates schematically a fifth embodiment of a processing system for the production of fatty acid alkyl esters according to an aspect of the presently disclosed subject matter.

Referring to FIG. 5, a modified second embodiment of the processing system, also referred to herein as the fifth embodiment and designated with the reference number 200', comprises all the elements and features of the second embodiment, including alternative variations thereof, including all like-numbered components as in FIG. 2, mutatis mutandis, with some differences. For example processing system 200' also comprises: a reactor vessel 120, a pre-reaction preparation vessel 140, a product separation vessel 160, supply of fatty acid source 182, alcohol source 184, optional buffer/water source 186, supply lines 152, 154, 156, vessel inlets 172, 174, 176, stirring system 142, outer jacket 149, outlet line 148 vessel inlet 121, stirring system 124, biocatalyst BC outer jacket 129, inlet and exit ports 123, outlet 127, filter 125, outlet line 147 (including lines 147A and 147B) first outlet interface 162 second outlet 164, valve 167A, valve 168A, first recirculation line 170; as disclosed for the second embodiment, mutatis mutandis.

However, in the fifth embodiment, tap 163 and valve 166 of the second embodiment are omitted, and instead a second embodiment of the auxiliary reactor module, designated with the reference numeral 300', is operatively connected to the first outlet interface 162 of the product separation vessel 160.

Auxiliary reactor module 300' is similar to auxiliary reactor module 300 of the fourth embodiment, and thus also comprises an auxiliary reactor vessel 220 and an auxiliary product separation vessel 260, which in this embodiment are thus also respectively substantially similar to reactor vessel 120 and product separation vessel 160, mutatis mutandis. In operation, the desired product P from product separation vessel 160 is routed to the auxiliary reactor vessel 220 via line 267 (which connects to first outlet interface 162), valve 226 and vessel inlet 221. When routed to auxiliary reactor vessel 220, the product P can be further reacted therein with alcohol AL (optionally in the presence of at least one of water (free or mixed with a polyol/polyols e.g. glycerol at different ratios) and aqueous buffer solution), provided via a separate line (not shown) from source 184 or from a different alcohol source (not shown), to produce further reacted products FRP. Line 247 enables the further reacted products FRP to be transported from vessel outlet 227 to the auxiliary product separation vessel 260, which then operates to separate a higher yield of product P' from byproducts, which can be removed via valve 266 and tap 263. As with the reactor vessel 120, mutatis mutandis, the vessel outlet 227 is spaced from the vessel inlet 221 in a direction opposed to the gravitational gradient.

However, auxiliary reactor module 300' further comprises recirculation line 270 provided via line 247A (which is part of line 247), line 265A valve 267A, and line 271, which are respectively similar to recirculation line 170, line 147A, line 165A valve 167A, and line 171 processing system 100', mutatis mutandis. Recirculation line 270 thus allows further reacted products FRP to be selectively re-routed to the reaction vessel 220 to further enhance the yield of product P in further reacted products FRP, rather than being channeled to the auxiliary product separation vessel 260, in a similar manner to the operation of recirculation line 170 of the reaction vessel 120, mutatis mutandis.

Processing system 200' can be operated in a similar manner to processing system 100', mutatis mutandis, with the main difference being that the product P, instead of being collected via tap 163 is further processed in auxiliary reaction vessel 220, and the further reacted products FRP are then transported to separation vessel 260. Optionally, the further reacted products FRP can be re-routed to reaction vessel 220 for as many recirculation cycles as desired via recirculation line 270, and eventually the further reacted products FRP are transported to separation vessel 260. In the separation vessel 260 the desired enhanced yield product P (fatty acid alkyl ester) in the further reacted products FRP are separated from by-products including excess water and glycerol G', and the enhanced yield product P' is then collected via tap 263.

It is to be noted that the processing system 100 according to the first embodiment, and/or the processing system 100" according to the third embodiment, can each be optionally modified to include auxiliary reactor module 300', in a similar manner to that disclosed herein for the second embodiment of the processing system 100' in the fifth embodiment of the processing system 200', mutatis mutandis, in which, essentially, in each case the respective valve 166 and tap 163 are removed, and replaced with auxiliary reactor module 300'.

In alternative variations of the embodiments of auxiliary reactor module 300 and/or auxiliary reactor module 300', an additional recirculation line can be provided to selectively channel the enhanced yield product P away from the respective tap 263 and into the respective auxiliary reaction vessel 220 via a respective recirculation line, for example similar to recirculation line 175 with respect to product P and reaction vessel 120, as disclosed herein, mutatis mutandis.

It is appreciated that all components of the processing system according to the first, second, third, fourth or fifth embodiments, or alternative variations thereof, are of a suitable form and made from suitable materials as known in the art, such as to enable each component to carrying out the respective functions at the respective conditions, including temperature, pressure, pH and so on.

Processes for transesterification/esterification of a fatty acid source with an alcohol in the presence of immobilized lipase/s, can be carried out in the processing system disclosed herein, under specific conditions which enable preservation of the stability of the immobilized lipase/s over scores of production cycles.

In an embodiment of the presently disclosed subject matter, the presently disclosed subject matter relates to a process for the transesterification/esterification of a fatty acid source with an alcohol, to form fatty acid alkyl esters, comprising reacting a reaction medium including a fatty acid source and an alcohol or an alcohol donor in the presence of an immobilized lipase preparation, wherein the immobilized lipase preparation comprises at least one lipase immobilized on a hydrophobic porous support and the reaction medium optionally contains at least one of an aqueous alkaline buffer solution and water, and wherein the reaction medium is passed through said immobilized lipase preparation in a direction at least partially opposed to gravity.

In the disclosed process, the alkyl esters can be short-chain alkyl esters of fatty acids, such as fatty acid methyl and ethyl esters (biodiesel).

In some embodiments of the disclosed process, the reaction can optionally be carried out in the presence of at least one of (1) an aqueous buffer, specifically an alkaline buffer, more specifically a mild alkaline buffer and (2) water, free or mixed with polyol/polyols e.g. glycerol, at different ratios. The fatty acid source can be pretreated with the alkaline buffer solution. Without being bound by theory, it is suggested that such pretreatment would result in neutralizing acids that might have an inhibitory effect on the enzyme. The quantity of the at least one of alcohol or alcohol donor and water required to complete the reaction up to 100% conversion can be added stepwise or in a one batch. Further, the alcohol can be short-chain alcohol, for example methanol or ethanol. Other alcohol donors can be used in the reaction with the fatty acid source in the presence of a hydrolase preparation and allowing the reaction to proceed under suitable conditions, until said fatty acid source is converted to fatty acid alkyl esters, specifically, fatty acid methyl esters (FAME) or fatty acid ethyl esters, wherein said hydrolase preparation comprises one or more lipases, separately or jointly immobilized on a suitable macroreticular porous hydrophobic polymer-based support.

The terms "buffer" "aqueous buffer" "buffer solution" and "aqueous buffer solution" are used herein synonymously.

By water as used herein is meant pure or distilled water. Also referred to herein as "free water", substantially free of solutes, and also "water solutions" (also referred to as aqueous solutions), which can be, but are not limited to, tap water, sea water or water from any other natural water resource or reservoir, desalinated water, chemically or enzymatically purified or treated water, and any other aqueous solutions, for example dissolved salts solutions. The pH of the reaction processing system or of the water solution can vary, and can be, for example, about 3-11, for example 4-10, 5-10, 5-9, 6-10, 6-9, or 7-9.

In the disclosed process, the at least one of aqueous buffer and water, free or mixed with a polyol/polyols e.g. glycerol at different ratios, can be added at an amount of at least 0.0001% wt. (on basis of the fatty acid source). Suitable ratios range from 1:99 to 99:1 water:plyol/glycerol.

As described above, the process of the presently disclosed subject matter can be carried out while continuously removing the formed glycerol and any excess water from the reaction mixture. The conversion of the fatty acid acyl groups or free fatty acids comprised in said fatty acid source to fatty acid alkyl, specifically methyl esters can be monitored at various time points during the reaction. The reaction medium can be removed by suitable means at any desired time point during the reaction, thereby stopping the reaction, and the formed fatty acid methyl esters and optionally the formed glycerol are isolated from the reaction medium. The reaction can be specifically stopped when the conversion of the fatty acid acyl groups or free fatty acids comprised in said fatty acid source to fatty acid methyl esters has reached at least 70%, for example at least 85%, or at least 90%.

Percentages are generally weight percents, unless indicated otherwise.

For example, the production processing system can use a reaction vessel 120 in the form of a stirred tank reactor with an upper filter 125 in the form of sintered glass, wedge wire filter, wedge wire nozzles or stainless steel filter which retains the biocatalyst in the reactor, however allows the reaction medium to permeate through out of the reactor. Such reactor configuration allows by-products, specifically glycerol and water, which are self-desorbed from the immobilized enzyme, to be moved through the reaction a direction opposed to gravity, together with the reaction mixture, and to permeate out through the filter 125 and out the upper outlet 127. The result is continuous removal of the desorbed formed glycerol and also of excess water, out of the reaction medium, leading to shift of the reaction towards synthesis, thereby reaching conversions above 96%. The biocatalyst used in this reactor can be comprised of a single or multi-types of lipases, in consideration of their positional specificity as well as their origin, as described herein. Alternative, two or more consecutive reactor vessels in the form of stirred tank reactors, each with an upper filter can be used. A product separation vessel 160 for example in the form of a settling tank or centrifuge can be used between each consecutive pair of reactor vessels. The first reactor vessel can contain an immobilized biocatalyst comprised of a single or multi-types of lipases. The role of the settling tank or centrifuge between each consecutive pair of reactor vessels is to remove the formed glycerol and excess water from the reaction medium, leading to an increase in the conversion of the raw materials to their corresponding fatty acid alkyl esters to above 96% in the second reactor at reasonable reaction time. Some specific reaction processing systems and methods are described below.

The terms "reaction mixture" and "reaction medium" can be used herein synonymously.

The use of lipases immobilized on solid insoluble resins, specifically solid insoluble hydrophobic resins, optionally in the presence of alkaline buffer solution or water, free or mixed with polyol/polyols such as glycerol at different ratios as described above, as in embodiments of the process of the presently disclosed subject matter, ensures high stability of the enzyme and also avoidance of the accumulation of hydrophilic substances, such as water and the formed glycerol by-product, on the biocatalyst. In all aspects and embodiments of the process of the presently disclosed subject matter in which alkaline or mild alkaline buffer is used, it can be used in more than 0.001% wt. (of the fatty acid source) alkaline or mild alkaline buffer solution, for example, but not limited to 0.01-50%, 0.05-50%, 0.1-50%, 0.5-50%, 1-50%, 1-45%, 1-40%, 1-35%, 1-30%, 1-25%, 1-20%, 1-15%, 1-10%, 1-8%, such as but not limited to more than 0.001%, 0.01%, 0.05%, 0.1%, 0.5%, 0.75%, 1%, 1.5%, 2%, 2.5%, 3%, 3.5%, 4%, 4.5%, 5%, 6%, 7%, 8%, 10%, 12%, 15%, 20%, 25%, 30%, 35%, 40%, 45%, 50%, 60%, or 70%. Levels of the alkaline or mild alkaline buffer solution can be up to 99% wt. In all aspects and embodiments of the presently disclosed subject matter where water or water solution are used, the water or water solution (such as water containing polyol/polyols such as glycerol and/or sugar at different ratios as described above) is used at levels of, but not limited to, more than 0.0001%, for example 0.0001-50%, 0.001-50%, 0.1-50%, 0.0001-30%, 0.001-30%, 0.1-30%, 0.0001-20%, 0.001-20%, 0.1-20%, such as but not limited to more than 0.0001%, 0.001%, 0.01%, 0.05%, 0.1%, 0.5%, 0.75%, 1%, 1.5%, 2%, 2.5%, 3%, 3.5%, 4%, 4.5%, 5%, 6%, 7%, 8%, 10%, 12%, 15%, 20%, 25%, 30%, 35%, 40%, 45%, 50%, or 70%. Water or water solution levels in the reaction mixture can be up to 99% wt. As mentioned, it is suggested that when alkaline solution is used, it can neutralize acids typically present in the fatty acid source or produced due to side reactions. Continuous active removal of these by-products can further increase the efficiency of the process. The isolated glycerol can be industrially used.

The fatty acid source is at least one of triglycerides, partial glycerides, free fatty acids, phospholipids, esters and amides of fatty acids or a mixture comprised of at least two said sources. More specifically, the fatty acid source used in the process of the presently disclosed subject matter can comprise at least one of soybean oil, canola oil, algae oil, rapeseed oil, olive oil, castor oil, palm oil, sunflower oil, peanut oil, cotton seed oil, Jatropha oil, crude corn oil, fish oil, animal-derived fat, waste cooking oil, brown grease, oil triglycerides derived from inedible plant sources, partial glycerides and free fatty acids derived from those oils or any mixture of at least two thereof, at any desired ratio.

In all processes of the presently disclosed subject matter, the fatty acid short-chain alkyl esters formed by the reaction are specifically fatty acid methyl, ethyl, iso-propyl or butyl esters (biodiesel). Other medium-chain fatty alcohols ($C_6$-$C_{10}$) and long-chain fatty alcohols ($C_{12}$-$C_{22}$) might also be used in the process of production of this presently disclosed subject matter. These longer alcohols can be specifically suitable in the production of waxes, for example for cosmetic products.

The lipases can be lipases derived from *Rhizomucor miehei*, *Mucor miehei*, *Pseudomonas* sp., *Rhizopus* sp., *Mucor javanicus*, *Penicillium roqueforti*, *Aspergillus niger*, *Thermomyces lanuginosus*, *Chromobacterium viscosum*, *Acromobacter* sp., *Burkholderia* sp., *Candida antarctica* A, *Candida antarctica* B, *Candida rugosa*, *Alcaligenes* sp., *Penicillium camembertii*, papaya seeds and pancreatin, but are not limited thereto.

The lipases can be jointly immobilized on a suitable support, specifically a hydrophobic aliphatic polymer-based support or a hydrophobic aromatic polymeric support. Additionally and alternatively, when more than one lipase is used, each said lipase can be immobilized on a suitable support, wherein the supports on which the said lipases are immobilized are identical or different. Lipases employed can be regio-specific to their substrate, or random. Lipases co-immobilized on the same support can exhibit identical or different substrate selectivities or regio-specificities to their substrates. Lipases can be regio-specific (or site-specific), each used alone or in combination with lipases of same or different site specificity. When referring to positions sn-1, sn-2 or sn-3 positions, these are positions on the glycerol backbone of the various glycerides. Thus, the lipases used in the process of the presently disclosed subject matter can possess selectivity towards sn-2 position higher than that of random lipases, i.e. they favour catalyzing the reaction between the alcohol or alcohol donor with the fatty acyl group of the sn-2 position, while random lipases exhibit the same transesterification activity for fatty acyl groups at all three positions on the glycerol backbone. Some lipases uniquely exhibit positional activity on sn-2 position, especially under specific conditions determined by the substrates, products, etc. Other lipases used in the process of the presently disclosed subject matter are sn-1,3 positional specific. They can be used alone or together with a random lipase, specifically lipase that has affinity to partial glycerides, and optionally a third lipase with a high affinity to the sn-2 position.

The support is specifically a porous and macroreticular hydrophobic support, which can be organic or inorganic. Examples of supports are porous inorganic supports, such as, but not limited to hydrophobized silica- or alumina-based supports, and hydrophobic organic supports such as, but not limited to polymeric or polymer-based support. The supports can optionally contain active functional groups selected from epoxy or and aldehyde groups, or ionic groups.

Specific insoluble supports used in the processes of the presently disclosed subject matter can be porous and reticular hydrophobic aliphatic or aromatic polymer-based supports, such as Amberlite® XAD 1600 and Sepabeads® SP70 both comprised of porous macroreticular resin prepared from divinylbenzene or from a mixture of divinylbenzene and polystyrene, Amberlite® XAD 7HP comprised of macroreticular aliphatic acrylic polymer, and porous aliphatic polymer such as porous polypropylene (Accurel®). Other specific supports can be a reticular hydrophobic polymer comprised of divinylbenzene, or a mixture of divinylbenzene and styrene, and reticular hydrophobic aliphatic polymer comprised of aliphatic acrylic polymers or polyalkene, such as polypropylene. Specific supports are porous matrices, of pore size in the range of 25-1000 Å, and more specifically in the range of 80-200 Å. The support also can be powderous or granular porous hydrophobic silica or other inorganic oxides. The support also can be powderous or granular porous hydrophobicized silica or other inorganic oxides. In specific embodiments, the surface area of the support resins is higher than 100 $m^2/g$. It can be noted that resins of hydrophilic nature tend to adsorb glycerol and water, leading to clogging of the reactor system.

The amount of the alkaline or mild alkaline aqueous buffer solution or water, free or mixed with a polyol/polyols such as glycerol at different ratios as described above, to be supplemented into the lipase catalyzed transesterification/esterification reaction between the fatty acid source and the alcohol is generally adjusted in accordance with the other reaction conditions, starting materials, biocatalyst, etc. This amount can be varied, as recited and exemplified herein. This alkaline solution is prepared, for example, from an inorganic alkaline base or salt or from an organic base. Inorganic bases and salts are, for example, alkaline metal hydroxides, carbonates, bicarbonates, phosphates, sulfates, acetates and citrates. Organic bases can be, for example, primary, secondary or tertiary amines, or polyol/polyols such as glycerol, propylene glycols and sugars. Mixtures of these alkaline agents are also contemplated. In embodiments of the process according to the presently disclosed subject matter, the pH of the microenvironment of the immobilized enzyme can be maintained at pH values of 5.5-5.9.

The production of fatty acid alkyl esters is carried out by transesterification or esterification, simultaneously or sequentially. Under such reaction processing system the biocatalyst activity is maintained with no significant activity losses in multiple uses and also avoids the accumulation of glycerol and water by-products or other hydrophilic compounds on the biocatalyst.

The presently disclosed subject matter provides processes employing specific immobilized interfacial enzymes that retain high activity and stability over many production cycles. Specifically, lipases and phosphor-lipases preparation are used, in transesterification/esterification reactions. These reactions can be employed in the production of food articles, cosmetics and biofuels ("biodiesel"). Of particular interest, these enzymes can be used for the synthesis of fatty acids short-chain alkyl esters for use as "biodiesel".

The presently disclosed subject matter employed stable immobilized interfacial enzymes, of high tolerance towards short-chain alcohols, such as methanol, ethanol and glycerol, as well as short-chain fatty acids, such as acetic acid. The use of these enzyme preparations also prevents accumulation on the immobilized biocatalyst of hydrophilic substances, in particularly glycerol and water.

The alcohol or alcohol donor employed in the processes of the presently disclosed subject matter can be a short-chain alkyl alcohol, specifically $C_1$-$C_6$ alkyl alcohol, more specifically $C_1$-$C_4$ alkyl alcohol, and particularly methanol or ethanol or the alcohol donor can be mono-alkyl ester or dialkyl carbonate, such as dimethyl carbonate. An alcohol donor such as for example dialkyl carbonate can also serve as a source for alkalinity or mild alkalinity of the reaction processing system.

Disclosed and described, it is to be understood that this presently disclosed subject matter is not limited to the particular examples, process steps, and materials disclosed herein as such process steps and materials can vary somewhat. It is also to be understood that the terminology used herein is used for the purpose of describing particular embodiments only and not intended to be limiting since the scope of the presently disclosed subject matter, will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the presently disclosed subject matter. It should be appreciated that while these techniques are exemplary of embodiments for the practice of the presently disclosed subject matter, those of skill in the art, in light of the present disclosure, will recognize that numerous modifications can be made without departing from the intended scope of the presently disclosed subject matter.

EXAMPLES

Materials and Methods
Lipase Immobilization:
Lipases were immobilized following standard procedures, such as those disclosed in applicant's WO2011/107977, incorporated herein by reference. Briefly, a lipase derived from a specific source, such as a microorganism, is solubilized in buffer solution of 0.1M at a suitable pH value, typically 7.5. A hydrophobic organic or inorganic polymer resin is added into the lipase solution. The mixture is shaken at room temperature for 8 hour. The mixture is then filtered and the immobilized enzyme is dried to reduce the water content to less than 10%.

Different resins were used, including porous hydrophobic polymer resins based on polystyrene/divinyl-benzene, paraffin or any of their combinations. Typical hydrophobic resins used included porous macroreticular divinyl-benzene/polystyrene (DVB-PS) resin such Amberlite® XAD 1600 (Rohm & Haas, USA) and Sepabeads® SP70 (Resindion, Italy), or other equivalent resins.

Lipases derived from *Alcaligenes* sp. (AL), *Pseudomonas* sp. (PS) and *Thermomyces lanuginosa* (TL) immobilized on porous DVB-PS as a hydrophobic resin were used for the transesterification/esterification reactions of different feedstocks, which included refined or crude plant oils, animal fat, waste-cooking oil, grease trap, or any combination of such feedstocks, regardless of the FFA (free fatty acid) value of the feedstock.

All transesterification/esterification reactions experiments were conducted in a processing system including a reactor vessel in the form of a glass reactor which can be operated as batch or continuous reactor of the type expanded bed, fluidized bed or stirred tank reactor with flow through the reactor vessel in a direction generally aligned with gravity (top-bottom) or in a direction generally opposed to gravity (bottom-top). The reactor vessel in each case was also operated under mechanical stirring conditions. The reactor vessel dimensions were as follows:

Internal diameter: 10 cm
Height: 27 cm
Volume of reaction: 2120 ml

Example 1

In this example, three processing systems were tested for a period extending to not less than 262 days.

The first system (herein Example 1(a)) was based on the embodiment of the processing system 100' illustrated in FIG. 2 with flow through the reactor vessel 120 in a direction generally opposed to gravity (bottom to-top), and operated at a flow rate of 20 ml/min throughput through the processing system.

The second system (herein Example 1(b)(i)) served as a control, and was based on a processing system similar to the system 100 of FIG. 1, but with the flow through the reactor vessel in a direction generally aligned with gravity (top-to bottom), rather than in a direction generally opposed to gravity (bottom to-top), and operated at a flow rate of 20 ml/min throughput through the respective processing system.

The third system (herein Example 1(b)(ii)) also served as a control, and was based on a processing system similar to the second system (i.e., with the flow through the reactor vessel in a direction generally aligned with gravity (top-to bottom)) and operated at a reduced flow rate of 10 ml/min throughput through the processing system.

Example 1(a)

Transesterification/esterification of soybean oil or other feedstocks (regardless of the initial FFA value) with methanol were used to form biodiesel (and glycerol/water) using a system corresponding to processing system 100' according to the second embodiment of the presently disclosed subject matter (see FIG. 2), including the above-mentioned reactor vessel 120 in the form of a glass reactor. The various components of reaction system 100' will be referred to below in the examples.

Reaction Conditions:

Referring to the system of FIG. 2, Soybean oil (1680 g) containing 84 g of 0.1M sodium bicarbonate solution and methanol (125 g) were first premixed in pre-reaction preparation vessel 140 to form an emulsion, which was then introduced to the reactor vessel 120. The reaction mixture was mixed in the reactor vessel 120 with a lipase derived from *Thermomyces lanuginosa* immobilized on a hydrophobic and porous polystyrene-divinyl-benzene-based resin (500 g) for 6 hours at 30° C. The reaction mixture was filtered off through the upper filter 125 and fed via outlet 127 to product separation vessel 160. Glycerol and excess of water were removed from the reaction mixture in the product separation vessel 160.

Continuous Mode Reaction

To initialize the continuous process, the following was first carried out. The upper phase generated in the earlier stage in vessel 120 containing the fatty acid methyl esters and any unreacted glycerides was re-introduced to the reactor vessel via rerouting line, and stirring in the reactor vessel was resumed after the addition of methanol (125 g) and 84 g 0.1M sodium bicarbonate solution into the reaction medium in the reactor vessel.

The conversion to methyl esters after 2 hours was 87%. Continuous operation of the processing system was then carried out as follows. An emulsified reaction medium (prepared emulsion) containing soybean oil (80% wt), methanol (15%) and 0.1M sodium bicarbonate solution (5%) was continuously fed into the reactor vessel 120 at a flow rate of 20 ml/min. The reaction medium outputted from the outlet 127 at the upper part of the reactor was recirculated to the reactor 120 via feed line 170 to the lower part of the reactor vessel 120 (see FIG. 2) at a through flow rate of 100 ml/min, while maintaining the reaction mixture stirred by a propeller at 120 rpm. The flow rate of 100 ml/min in the recirculation line 170 was adequate in order to expand the enzyme bed. The temperature of the reaction medium was maintained at 30° C. The conversion to fatty acid methyl esters in a continuous system under such reaction conditions was maintained to more than 3 months without significant activity losses when using the same batch of biocatalyst derived from *Thermomyces lanuginosa* lipase immobilized on a macroporous hydrophobic resin.

Table 1, column 2 shows the conversion of feedstock to fatty acid methyl esters in the above system at a number of days during the 262 day trial.

Example 1(b(i))

The system, reaction conditions and continuous reaction mode of operation used for this example was similar to that of Example 1(a), mutatis mutandis, the only differences being as follows in Example 1(b)(i):

The product (1680 g) collected from vessel 160 was mixed with methanol (125 g) and sodium bicarbonate solution of 0.1M (84 g)

The reaction medium was not recirculated into the reaction vessel.

Continuous operation of the processing system was then carried out as follows. An emulsified reaction medium (prepared emulsion) containing soybean oil (80% wt), methanol (15%) and 0.1M sodium bicarbonate solution (5%) was continuously fed into the reactor vessel at the upper part of the reactor at a flow rate of 20 ml/min, while maintaining the reaction mixture stirred by a propeller at 120 rpm. The temperature of the reaction medium was maintained at 30° C. The conversion to fatty acid methyl esters under such reaction conditions was maintained for more than 7 months without significant activity losses when using the same batch of biocatalyst derived from *Thermomyces lanuginosa* lipase immobilized on a macroporous hydrophobic resin.

Table 1, column 3 shows the conversion of feedstock to fatty acid methyl esters in the above system at a number of days during the 262 day trial.

Example 1(b(ii))

The system, reaction conditions and continuous reaction mode of operation used for this example was similar to that of Example 1(b)(i), mutatis mutandis, the only differences being that in Example 1(b)(ii) an emulsified reaction medium (prepared emulsion) containing soybean oil (80% wt), methanol (15%) and 0.1M sodium bicarbonate solution (5%) was continuously fed into the reactor vessel at a flow rate of 10 ml/min rather than 20 ml/min (provided by example 1(b(i)) or example 1(a)).

Table 1, column 4 shows the conversion of feedstock to fatty acid methyl esters in the above system at a number of days during the 262 day trial

TABLE 1

The conversion of feedstock to fatty acid methyl esters in a continuous hybrid stirred- and expanded-bed reactor with time VS. control reactor vessel at the same flow rate and at reduced flow rate.

| Time (Days) | Conversion (%) hybrid stirred- and expanded-bed reactor at flow rate of 20 ml/min (Example 1(a)) | Conversion (%) Control reactor at flow rate of 20 ml/min (Example 1(b)(i)) | Conversion (%) Control reactor at flow rate of 10 ml/min Example 1(b)(ii) |
|---|---|---|---|
| 1 | 87 | 72 | 83 |
| 2 | 86 | 70 | 81 |
| 3 | 86 | 69 | 80 |
| 4 | 87 | 69 | 82 |
| 5 | 87 | 66 | 84 |
| 7 | 86 | 67 | 80 |
| 10 | 85 | 70 | 82 |
| 13 | 85 | 72 | 82 |
| 20 | 86 | 74 | 82 |
| 30 | 85 | 65 | 83 |
| 41 | 86 | 69 | 81 |
| 53 | 86 | 71 | 80 |
| 62 | 87 | 66 | 80 |
| 85 | 86 | 69 | 81 |
| 100 | 86 | 70 | 81 |
| 120 | 85 | 67 | 82 |
| 162 | 86 | 65 | 83 |
| 187 | 86 | 68 | 84 |
| 205 | 85 | 70 | 83 |
| 225 | 85 | 71 | 83 |
| 262 | 85 | 69 | 80 |

Example 2

Second Stage Transesterification/Esterification Reaction Using the Effluent of the First Stage In this example, three processing systems were tested for a period extending to not less than 121 days.

The first system (herein Example 2(a)) was based on the system 200' of FIG. 5 with flow thorough the reactor vessel 120 and in the auxiliary reactor vessel 220 was in a direction generally opposed to gravity (bottom to-top), and operated at a flow rate of 20 ml/min throughput through the system 200'.

The second system (herein Example 2(b)(i)) served as a control, and was based on a processing system similar to the system 200' of FIG. 5, but with the flow through the reactor vessel 100, and in the auxiliary reactor vessel 220 being in a direction generally aligned with gravity (top-to bottom), rather than in a direction generally opposed to gravity (bottom to-top), and operated at a flow rate of 20 ml/min throughput through the respective system.

The third system (herein Example 2(b)(ii)) was based on a processing system similar to the second system of example 2 (i.e., with the flow through the reactor vessel 100, and in the auxiliary reactor vessel 220 being in a direction generally aligned with gravity (top to-bottom)) and operated at a reduced flow rate of 10 ml/min throughput through the respective system.

Example 2(a)

Transesterification/esterification of the unreacted glycerides and free fatty acids of upper phase of the effluent separated in vessel 160 with methanol were used to form biodiesel glycerol/water using a system corresponding to processing system 200' according to the fifth embodiment of the presently disclosed subject matter (see FIG. 5), including the above-mentioned reactor vessel 120 and the auxiliary reactor vessel 220, each in the form of a glass reactor. The various components of reaction system 200' will be referred to below in the examples.

Reaction Conditions:

Referring to the system of FIG. 5, the upper phase of the effluent from the Reactor Vessel 120 separated in separation vessel 160 comprised of fatty acid methyl esters (above 80%) and unreacted glycerides and free fatty acids (1680 g) containing 33.6 g of 0.1M sodium bicarbonate solution and methanol (125 g) were introduced into the reactor vessel 220. The reaction mixture was mixed in the reactor vessel 220 with a lipase derived from *Thermomyces lanuginosa* immobilized on a hydrophobic and porous polystyrene-divinyl-benzene-based resin (500 g) for 30 minutes at 30° C.

Continuous Mode Reaction

Continuous operation of the processing system was then carried out as follows. An emulsified reaction medium (prepared emulsion) comprised of the upper phase obtained from the effluent of the reactor vessel 120 obtained in separation vessel 160, mixed with 7% methanol and 2% 0.1M sodium bicarbonate solution was prepared as in Example 1(a) and subsequently continuously fed into the auxiliary reactor vessel 220 at a flow rate of 20 ml/min. The reaction medium outputted from the outlet 227 at the upper part of the reactor 220 was recirculated to the auxiliary reactor vessel 220 via feed line 270 to the lower part of the auxiliary reactor vessel 220 at a through flow rate of 100 ml/min, while maintaining the reaction mixture stirred by a propeller at 120 rpm. The temperature of the reaction medium was maintained at 30° C. The conversion to fatty acid methyl esters in a continuous reaction mode under such reaction conditions was maintained for more than 3 months without significant activity losses when using the same batch of biocatalyst derived from *Thermomyces lanuginosa* lipase immobilized on a macroporous hydrophobic resin.

Table 2, column 2 shows the conversion of feedstock to fatty acid methyl esters in the above system at a number of days during the 121 day trial.

Example 2(b(i))

The system, reaction conditions and continuous reaction mode of operation used for this example was similar to that of Example 2(a), mutatis mutandis, the only differences being as follows in Example 2(b)(i):

The reaction medium was not recirculated into the reaction vessel.

The reaction medium was not recirculated into the auxiliary reaction vessel.

The emulsified reaction medium (prepared emulsion) comprised of the upper phase obtained from the effluent of the respective reactor vessel and the respective separation vessel, mixed with 7% methanol and 2% 0.1M sodium bicarbonate solution was continuously fed into the respective auxiliary reactor vessel at a flow rate of 20 ml/min at the top of the reactor.

The flow of the reaction medium in the reactor is from top to bottom.

Table 2, column 3 shows the conversion of feedstock to fatty acid methyl esters in the above system at a number of days during the 121 day trial.

Example 2(b(ii))

The system, reaction conditions and continuous reaction mode of operation used for this example was similar to that of Example 2(b)(i), mutatis mutandis, the only differences being that in Example 2(b)(ii) the emulsified reaction medium (prepared emulsion) comprised of the upper phase obtained from the effluent of the respective reactor vessel obtained in separation vessel 160, mixed with 7% methanol and 2% sodium bicarbonate solution of 0.1M was continuously fed from top to bottom into the reactor vessel and into the auxiliary reactor vessel (also from top to bottom) at a flow rate of 10 ml/min throughput, rather than 20 ml/min (provided by example 2(b)(i)) or example 2(a)).

Table 2, column 4 shows the conversion of feedstock to fatty acid methyl esters in the above system at a number of days during the 121 day trial.

TABLE 2

The conversion of feedstock to fatty acid methyl esters in a continuous hybrid stirred- and expanded-bed reactor with time

| Time (Days) | Conversion (%) hybrid stirred- and expanded-bed reactor at flow rate (20 ml/min) (Example 2(a)) | Conversion (%) Control reactor at flow rate (20 ml/min) (Example 2(b)(i)) | Conversion (%) Control reactor at flow rate (10 ml/min) (Example 2(b)(ii)) |
|---|---|---|---|
| 1 | 97 | 91 | 95 |
| 2 | 97.6 | 92 | 94 |
| 3 | 97.3 | 91 | 94 |
| 5 | 96 | 90 | 96 |
| 6 | 97.2 | 93 | 93 |
| 8 | 97.6 | 92 | 95 |
| 10 | 97.3 | 92 | 95 |
| 15 | 98.3 | 90 | 96 |
| 20 | 96 | 89 | 95 |
| 24 | 97.6 | 89 | 95 |
| 30 | 97.3 | 90 | 96 |
| 38 | 95.8 | 89 | 96 |
| 43 | 97.2 | 91 | 95 |
| 50 | 97.3 | 91 | 94 |
| 53 | 96.2 | 92 | 94 |
| 62 | 94.5 | 91 | 96 |
| 69 | 95.8 | 91 | 96 |
| 82 | 96.4 | 93 | 93 |
| 93 | 97.5 | 91 | 96 |
| 110 | 96 | 92 | 95 |
| 121 | 97 | 90 | 95 |

In order to produce biodiesel complying with the ASTM and EN specifications, the reaction effluent produced according to the presently disclosed subject matter, which typically contains more than 96% fatty acid methyl esters, 1-3% free fatty acids (FFAs), and 0.5-2% unreacted glycerides, can be post-treated, for example by following one of the below options:

1. Distillation of fatty acid methyl esters from the reaction mixture after phase separation and removal of water and excess methanol.
2. Treatment of the dehydrated reaction mixture after phase separation, with methanol and an esterification catalyst such as, but not limited to free or immobilized *Candida antarctica* lipase B, to convert unreacted FFAs and partial glycerides to fatty acid methyl esters.
3. Neutralization of FFAs with a base followed with water-wash.
4. Treatment of the reaction mixture after its flash evaporation with an adsorbent such as alkaline silicate, e.g. Magnesol®, to reduce FFA and partial glycerides content.
5. Treatment of the reaction mixture after its flash evaporation with an ionic-exchange resin to adsorb residual FFAs and partial glycerides.

The invention claimed is:

1. A process for the transesterification/esterification of a fatty acid source with an alcohol to form reaction products and by-products, said reaction products comprising fatty acid alkyl esters and said by-products comprising glycerol, in a reaction vessel comprising an inlet port and an outlet port, the process comprising:
   reacting, within the reaction vessel, a fatty acid source and an alcohol or an alcohol donor in a reaction medium that contains at least one of an aqueous alkaline buffer solution and water, free or mixed with polyol/polyols, in the presence of a lipase preparation that comprises at least one lipase immobilized on a hydrophobic porous support, by passing the reaction medium, containing the fatty acid source and the alcohol or alcohol donor, into the reaction vessel through the inlet port and through said lipase preparation in a gravity opposed direction while being mechanically stirred, and removing at least said glycerol by-product from the reaction vessel through the outlet port, wherein the inlet port is at a location on the reaction vessel lower than that of the outlet port.

2. The process according to claim 1, wherein the process further comprises the step of selectively directly recirculating said reaction products to said lipase preparation, and wherein, in said recirculating step, said reaction products are passed through said lipase preparation in a gravity-opposed direction-.

3. The process according to claim 2, comprising repeating said step of selectively directly recirculating reaction products of said reaction to said lipase preparation a plurality of times.

4. The process according to claim 1, further comprising the step of selectively separating said fatty acid alkyl esters from said reaction by-products.

5. The process according to claim 1, wherein said lipase preparation comprises at least two lipases which can be each separately immobilized on a hydrophobic support or co-immobilized on the same hydrophobic support, and wherein said lipases possess identical or different regio-specificity.

6. The process according to claim 1, wherein said support is any one of a hydrophobic aliphatic polymer-based support and a hydrophobic aromatic polymer-based support.

7. The process according to claim 1, wherein said support is a porous inorganic support, which can be hydrophobic or is coated with hydrophobic organic material.

8. The process according to claim 1, wherein said fatty acid source is selected from the group consisting of plant oil, animal fat, algal oil, fish oil, waste oil, brown grease and any mixtures thereof.

9. The process according to claim 1, wherein said fatty acid source comprises free fatty acids, mono-, di- or tri-glycerides, or their mixtures at any ratio.

10. The process according to claim 1, wherein said alcohol is methanol and said resulting fatty acid esters are fatty acid methyl esters.

11. A process for the transesterification/esterification of a fatty acid source with an alcohol to form reaction products and by-products, said reaction products comprising fatty acid alkyl esters and said by-products comprising glycerol, the process comprising:

reacting a fatty acid source and an alcohol or an alcohol donor in a reaction medium that contains at least one of an aqueous alkaline buffer solution and water, free or mixed with a polyol/polyols, in the presence of a lipase preparation that comprises at least one lipase immobilized on a hydrophobic porous support by passing the reaction medium, containing the fatty acid source and the alcohol or alcohol donor, through said lipase preparation in a gravity opposed direction, while being mechanically stirred, and wherein said process is conducted in a processing system comprising a reaction vessel configured for mechanically stirring the reaction medium and for passing the reaction medium, containing the fatty acid source and the alcohol or alcohol donor, through said lipase preparation in a gravity opposed direction, and wherein said reaction vessel comprises an inlet port and an outlet port, said inlet port being at a location on the reaction vessel lower than that of the outlet port, and wherein the reaction medium is fed into the reaction vessel through the inlet port and at least said glycerol by-product is removed from the reaction vessel through the outlet port.

12. The process according to claim 1, wherein said fatty acid source further comprises minor fatty acid derivatives selected from the group consisting of phospholipids and wax esters.

13. The process according to claim 1, wherein said fatty acid source is at least one of unrefined, refined, bleached or deodorized fatty acid sources.

14. The process according to claim 1, wherein said lipase preparation is granular.

15. The process according to claim 11, wherein said lipase preparation is granular.

16. The process according to claim 1, where said lipase preparation is in the form of beads.

17. The process according to claim 11, where said lipase preparation is in the form of beads.

18. The process according to claim 11, wherein said reaction vessel is configured for providing a stirred and expanded or stirred and fluidized bed of said lipase preparation.

19. A process for the transesterification/esterification of a fatty acid source with an alcohol to form reaction products and by-products, said reaction products comprising fatty acid alkyl esters and said by-products comprising glycerol, in a reaction vessel comprising an inlet port and an outlet port, the process comprising:

reacting, within the reaction vessel, a fatty acid source and an alcohol or an alcohol donor in a reaction medium that contains at least one of an aqueous alkaline buffer solution and water, free or mixed with polyol/polyols, in the presence of a granular lipase preparation that comprises at least one lipase immobilized on a hydrophobic porous support, by passing the reaction medium, containing the fatty acid source and the alcohol or alcohol donor, into the reaction vessel through the inlet port and through said lipase preparation in a gravity opposed direction while being mechanically stirred, and removing at least said glycerol by-product from the reaction vessel through the outlet port, wherein the inlet port is at a location on the reaction vessel lower than that of the outlet port.

20. A process for the transesterification/esterification of a fatty acid source with an alcohol to form reaction products and by-products, said reaction products comprising fatty acid alkyl esters and said by-products comprising glycerol, the process comprising:

reacting a fatty acid source and an alcohol or an alcohol donor in a reaction medium that contains at least one of an aqueous alkaline buffer solution and water, free or mixed with polyol/polyols, in the presence of a granular lipase preparation that comprises at least one lipase immobilized on a hydrophobic porous support, by passing the reaction medium, containing the fatty acid source and the alcohol or alcohol donor, through said lipase preparation in a gravity opposed direction, while being mechanically stirred, and wherein said process is conducted in a processing system comprising a reaction vessel configured for mechanically stirring the reaction medium, containing the fatty acid source and the alcohol or alcohol donor, and for passing the reaction medium through said lipase preparation in a gravity opposed direction, and wherein said reaction vessel comprises an inlet port and an outlet port, said inlet port being at a location on the reaction vessel lower than that of the outlet port, and wherein the reaction medium is fed into the reaction vessel through the inlet port and at least said glycerol by-product is removed from the reaction vessel through the outlet port.

21. The process according to claim 20, wherein said reaction vessel is configured for providing a stirred and expanded or stirred and fluidized bed of said lipase preparation.

* * * * *